United States Patent [19]

Dibiase et al.

[11] Patent Number: 5,786,506

[45] Date of Patent: Jul. 28, 1998

[54] PROCESS FOR DISTILLATION OF CRUDE ISOCYANATE CONCENTRATES

[75] Inventors: Stephen A. Dibiase, Euclid, Ohio; Larry W. Arndt, Pasedena; Gregory M. Stansfield, Seabrook, both of Tex.; Louis A. Renbaum, Pittsburgh, Pa.

[73] Assignees: The Lubrizol Corporation, Wickliffe, Ohio; Miles Inc., Pittsburgh, Pa.

[21] Appl. No.: 986,878

[22] Filed: Dec. 4, 1992

Related U.S. Application Data

[63] Continuation of Ser. No. 659,411, PCT/US90/00815 filed Feb. 21, 1990, abandoned, which is a continuation-in-part of Ser. No. 470,431, Jan. 24, 1990, abandoned, which is a continuation of Ser. No. 319,011, Mar. 3, 1989, abandoned.

[51] Int. Cl.$^6$ .................................................. C07C 251/00
[52] U.S. Cl. .................................................. 560/352
[58] Field of Search .................................................. 560/352

[56] References Cited

U.S. PATENT DOCUMENTS

| | | |
|---|---|---|
| 2,239,974 | 4/1941 | Reed et al. |
| 2,319,121 | 5/1943 | Fox |
| 2,337,552 | 12/1943 | Henke |
| 2,666,044 | 1/1954 | Catlin |
| 2,737,452 | 3/1956 | Catlin |
| 2,737,496 | 3/1956 | Catlin |
| 2,810,681 | 10/1957 | Nadler ........................ 203/38 |
| 2,889,257 | 6/1959 | Griffin et al. |
| 3,488,284 | 1/1970 | LeSuer et al. |
| 3,595,790 | 7/1971 | Norman et al. |
| 3,702,300 | 11/1972 | Coleman |
| 3,729,386 | 4/1973 | Irwin et al. |
| 3,804,763 | 4/1974 | Meinhardt |
| 3,948,800 | 4/1976 | Meinhardt |
| 3,957,854 | 5/1976 | Miller |
| 4,234,435 | 11/1980 | Meinhardt et al. |
| 4,326,972 | 4/1982 | Chamberlin |
| 5,043,470 | 8/1991 | Dibiase et al. ........................ 560/352 |

OTHER PUBLICATIONS

Sanders and Frisch: Polyurethanes: Chemistry and Technology I. Chemistry, Part I, pp. 17–28. Interscience Publishers, New York, New York 1962.

Ranney, "Lubricant Additives", Noyes Data Corporation, 1973, pp. 92–119.

*Primary Examiner*—Alan Siegel
*Attorney, Agent, or Firm*—Renner, Otto, Boisselle & Sklar

[57] ABSTRACT

A process is described for the separation and recovery of isocyanate monomers from isocyanate concentrates which leaves a residue which is liquid and burnable. The process for the separation and recovery of isocyanate monomers from isocyanate concentrates formed in the production of isocyanates and comprising a volatile isocyanate monomer and by-products comprises the steps of:

(A) preparing a mixture comprising
    (A-1) the isocyanate concentrate; and
    (A-2) an oil solution comprising:
        (A-2-a) a major amount of hydrocarbon oil, and
        (A-2-b) a minor amount of at least one ashless dispersant; and (B) heating the mixture to an elevated temperature at reduced pressure whereby isocyanate monomer is distilled and recovered leaving a liquid residue. The presence of the oil solution in the mixture facilitates the distillation of the isocyanate concentrate, generally improves the yield of distilled isocyanate monomer, results in a residue which is liquid and easily removed from the distillation apparatus, and the liquid residue can generally be burned without difficulty.

2 Claims, No Drawings

PROCESS FOR DISTILLATION OF CRUDE ISOCYANATE CONCENTRATES

CROSS-REFERENCE TO RELATED APPLICATIONS

This application is a continuation of application Ser. No. 07/659,411 filed Mar. 11, 1991 now abandoned which is a continuation of International Application No. PCT/US90/00815 filed Feb. 21, 1990 which is a continuation-in-part of Ser. No. 07/470,431 filed Jan. 24, 1990 now abandoned which is a continuation of Ser. No. 07/319,011 filed Mar. 3, 1989 now abandoned.

FIELD OF THE INVENTION

This invention relates to a process for recovering isocyanates from crude isocyanate concentrates. In particular, this invention relates to a process for separating and recovering isocyanate monomers from crude isocyanate concentrates formed from the production of isocyanates and comprising a volatile isocyanate monomer and by-products.

BACKGROUND OF THE INVENTION

Various methods for preparing isocyanates have been reported in the literature. An important commercial method for preparing isocyanates involves the phosgenation of primary amines. Isocyanates also can be prepared utilizing the Curtius rearrangement of an acid azide in a neutral solvent. The Curtius reaction is used primarily for the preparation of short chain aliphatic diisocyanates and unsaturated isocyanates. The Hofmann rearrangement of amides to form isocyanates is useful for preparing isocyanates which do not react with water since an aqueous medium is required. Another, less frequently used reaction, is the Lossen rearrangement of hydroxamic acids. The process can be exemplified by the preparation of octamethylene diisocyanate from the disodium salt of sebacic dihydroxamic acid. Other procedures for preparing isocyanate compounds are described in Saunders and Frisch: Polyurethanes:Chemistry and Technology I, Chemistry, Part I, pages 17–28, Interscience Publishers, New York, N.Y., 1962.

Considerable quantities of relatively high molecular weight, cross-linked, by-products are formed in these processes, particularly in the phosgene process. Generally, the by-products are obtained in the form of a tar-like, non-distillable residue during and after the distillation of the crude isocyanate concentrate solutions obtained in the phosgenation of amines.

In a commercial method for preparing diisocyanates, an amine solution is mixed with phosgene at a low or moderate temperature. The resulting slurry is heated to a higher temperature such as from about 120°–180° C., and the product is obtained by distillation. During the distillation of the concentrate, relatively high molecular weight insoluble products containing uretdione, isocyanurate, carbodiimide, uretone imine, urea and biuret groups are formed under the conditions of the distillation. The residue which remains after distillation are slag-like materials which are generally substantially insoluble in conventional solvents, and although considerable effort has been expended in developing uses for the residues, a vast majority of the distillation residues are either dumped or burned in furnaces with considerable difficulty. In those instances where the distillation residues have been burned, the deposits of firmly adhering, substantially non-flammable tarry masses often accumulate in the combustion chamber, and some of these tarry masses have decomposed explosively at temperatures above about 500° C.

U.S. Pat. No. 4,251,401 describes the preparation of stable suspensions of substantially monomer-free, insoluble, powdered tolylene diisocyanate distillation residues in polyhydroxy compounds. The suspensions are reported as being useful as the polyol component in the production of polyurethane plastics including foamed polyurethane plastics. U.S. Pat. No. 4,297,456 describes the process for working up the distillation residue obtained in the commercial production of tolylene diisocyanate by grinding, and optionally, accompanied and/or followed by chemical modification reactions. The finely divided powder is reported as being useful as a reactant filler in the production of a variety of plastics.

Other processes have been proposed for handling and disposing isocyanate distillation residues. In Col. 1 of U.S. Pat. No. 4,297,456, a number of patents and publications are described which relate to dissolving TDI distillation residues.

SUMMARY OF THE INVENTION

A process is described for the separation and recovery of isocyanate monomers from isocyanate concentrates which leaves a residue which is a liquid suspension and burnable. The process for the separation and recovery of isocyanate monomers from isocyanate concentrates formed in the production of isocyanates and comprising a volatile isocyanate monomer and by-products comprises the steps of:

(A) preparing a mixture comprising (A-1) the isocyanate concentrate; and (A-2) an oil solution comprising;

(A-2-a) a major amount of hydrocarbon oil, and (A-2-b) a minor amount of an ashless dispersant; and (B) heating the mixture to an elevated temperature whereby isocyanate monomer is distilled and recovered leaving a liquid residue.

In one preferred embodiment, the ashless dispersant of (A-2-b) comprises at least one carboxylic ester obtained by reacting (A-2-b-1) at least one substituted succinic acylating agent with (A-2-b-2) at least one alcohol of the general formula $$R_1(OH)_m \qquad (I)$$

wherein $R_1$ is a monovalent or polyvalent organic group joined to the OH groups through carbon bonds, and m is an integer of from 1 to about 10.

In another preferred embodiment, the oil solution (A-2) also contains (A-2-c) a minor amount of at least one neutral or basic alkali metal or alkaline earth metal salt of at least one acidic organic compound.

The presence of the oil solution in the mixture facilitates the distillation of the isocyanate concentrate, generally improves the yield of distilled isocyanate monomer, results in a residue which is a liquid suspension and easily removed from the distillation apparatus, and the liquid residue can be burned without difficulty.

DESCRIPTION OF THE PREFERRED EMBODIMENTS

It has now been discovered that isocyanate monomers can be recovered in high purity and in improved yields from crude isocyanate concentrates which comprise a volatile isocyanate monomer and by-products. In general, the process involves preparing a mixture comprising the crude isocyanate concentrate and an oil solution as described hereinafter, and heating the mixture to an elevated temperature, at a reduced pressure, whereby isocyanate monomer is distilled and recovered leaving a liquid residue.

The following definitions apply throughout this specification and claims unless clearly indicated otherwise.

The number of equivalents of the acylating agent depends on the total number of carboxylic functions present. In determining the number of equivalents for the acylating agents, those carboxyl functions which are not capable of reacting as a carboxylic acid acylating agent are excluded. In general, however, there is one equivalent of acylating agent for each carboxy group in these acylating agents. For example, there are two equivalents in an anhydride derived from the reaction of one mole of olefin polymer and one mole of maleic anhydride. Conventional techniques are readily available for determining the number of carboxyl functions (e.g., acid number, saponification number) and, thus, the number of equivalents of the acylating agent can be readily determined by one skilled in the art.

An equivalent weight of polyhydric alcohol is its molecular weight divided by the total number of hydroxyl groups present in the molecule. Thus, an equivalent weight of ethylene glycol is one-half its molecular weight.

An equivalent weight of an amine or a polyamine is the molecular weight of the amine or polyamine divided by the total number of nitrogens (or >NH groups) present in the molecule. Thus, ethylene diamine has an equivalent weight equal to one-half of its molecular weight; diethylene triamine has an equivalent weight equal to one-third its molecular weight. The equivalent weight of a commercially available mixture of polyalkylene polyamine can be determined by dividing the atomic weight of nitrogen (14) by the %N contained in the polyamine and multiplying by 100; thus, a polyamine mixture containing 34% nitrogen would have an equivalent weight of 41.2. An equivalent weight of ammonia or a monoamine is the molecular weight.

An equivalent weight of a hydroxyl-substituted amine to be reacted with the acylating agents to form the carboxylic derivative (B) is its molecular weight divided by the total number of >NH and —OH groups present in the molecule. Thus, ethanolamine would have an equivalent weight equal to one-half of its molecular weight, and diethanolamine has an equivalent weight equal to one-third of its molecular weight.

The equivalent weight of a hydroxyamine used to form the carboxylic esters (A-2-b) useful in this inven- tion is its molecular weight divided by the number of hydroxyl groups present, and the nitrogen atoms present are ignored. Thus, when preparing esters from, e.g., diethanolamine, the equivalent weight is one-half the molecular weight of diethanolamine.

The terms "substituent" and "acylating agent" or "substituted succinic acylating agent" are to be given their normal meanings. For example, a substituent is an atom or group of atoms that has replaced another atom or group in a molecule as a result of a reaction. The term acylating agent or substituted succinic acylating agent refers to the compound per se and does not include unreacted reactants used to form the acylating agent or substituted succinic acylating agent.

All parts and percentages are by weight, all temperatures are in degrees Celsius, and pressures are at or near atmospheric unless otherwise specifically indicated.

(A-1) The Crude Isocyanate Concentrate.

The crude isocyanate concentrates which can be treated in accordance with the present invention are concentrates obtained from the preparation of isocyanates prior to distillation. The concentrates contain large amounts of the isocyanates and minor amounts of by-products or secondary products. The process of this invention is applicable in particular to crude concentrates obtained by reacting amines with phosgene. The amines may be aliphatic amines, cycloaliphatic amines, aromatic amines, or mixed aliphatic-aromatic amines, and these amines may be monoamines or polyamines. In one preferred embodiment, the amines are primary amines.

The reaction between primary amines and phosgene is well known and is utilized for the commercial preparation of isocyanates. The reaction is illustrated as follows:

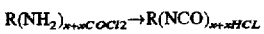

wherein x is an integer equal to the number of $NH_2$ groups present in the amine used in the reaction. For example, if the amine is a diamine (x=2), the diamine is reacted with two moles of phosgene and the product is a diisocyanate. In addition to the desired isocyanate, the product obtained contains a number of by-products including amine hydrochlorides, carbamoyl chlorides, substituted ureas, etc. It is this mixture that is referred to in the art and in this application as the crude isocyanate concentrate.

Monomeric isocyanates including diisocyanates and triisocyanates, which can be present in the crude isocyanate concentrates treated in accordance with the process of the present invention include hexamethylene diisocyanate, trimethylhexamethylene diisocyanate, naphthylene, trimethylhexamethylene diisocyanate, naphthylene-1,5-diisocyanate, tolylene-2,4-diisocyanate, tolylene-2,6-diisocyanate, mixtures of the tolylene 2,4-and 2,6-diisocyanates, 2,4'-and 4,4'-diisocyanato diphenylmethane and mixtures of these, dicyclohexylmethane-4,4'-diisocyanate, cyclohexyl isocyanate, stearyl isocyanate, phenyl isocyanate, o-, m- and p-tolyl isocyanate, o-, m-and p-chlorophenyl isocyanate, 3,4-dichlorophenyl isocyanate, 2,6-diisopropylphenyl isocyanate, 2,6-triisocyanato-1,3,5-triisopropyl benzene, etc. The residue which remains after distillation of the monomer from the crude isocyanate concentrate generally amounts to about 5–10% of the total isocyanate production. The process of the present application is particularly applicable to the distillation and recovery of tolylene diisocyanates (TDI).

(A-2) Oil Solution.

The oil solutions which are mixed with the isocyanate concentrate in accordance with the process of the present invention comprise (A-2-a) a major amount of oil, and (A-2-b) a minor amount at least one carboxylic ester.

The oil solution may also contain a minor amount of (A-2-c) at least one neutral or basic alkali metal or alkaline earth metal salt of at least one acidic organic compound.

(A-2-a) The Hydrocarbon Oil.

The hydrocarbon oil which is utilized in the preparation of the oil solutions (A-2) of the invention may be based on natural oils, synthetic oils, or mixtures thereof. The hydrocarbon oils may be of the type generally known as lubricating oils or fuel oils.

Natural oils include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinic-naphthenic types. Oils derived from coal or shale are also useful. Synthetic oils include hydrocarbon oils and halosubstituted hydrocarbon oils such as polymerized and interpolymerized olefins (e.g., polybutylenes, polypropylenes, propylene-isobutylene copolymers, chlorinated polybutylenes, etc.); poly(1-hexenes), poly(1-octenes), poly(1-decenes), etc. and mixtures thereof; alkylbenzenes (e.g., dodecylbenzenes, tetradecylbenzenes, dinonylbenzenes, di-(2-ethylhexyl)-benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic oils that can be used. These are exemplified by the oils prepared through polymerization of ethylene oxide or propylene oxide, the alkyl and aryl ethers of these polyoxyalkylene polymers.

Another suitable class of synthetic oils that can be used comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.) Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methylhexyl)silicate, tetra-(p-tert-butylphenyl)silicate, hexyl(4-methyl-2-pentoxy) disiloxane, poly(methyl)siloxanes, poly(methylphenyl) siloxanes, etc.). Other synthetic oils include liquid esters of phosphorus-containing acids (e.g., tricresyl phosphate, trioctyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those skilled in the art such as solvent extraction, hydrotreating, secondary distillation, acid or base extraction, filtration, percolation, etc. Rerefined oils are obtained by processes similar to those used to obtain refined oils applied to refined oils which have been already used in service. Such rerefined oils are also known as reclaimed, recycled, or reprocessed oils and often are additionally processed by techniques directed to removal of spent additives and oilbreakdown products.

(A-2-b) Ashless Dispersant.

The oil solutions used in the present invention contain at least one ashless dispersant. Ashless dispersants are referred to as being ashless despite the fact that, depending on their constitution the dispersants may upon combustion yield a non-volatile material such as boric oxide or phosphorus pentoxide. However, the ashless dispersants do not ordinarily contain metal, and therefore do not yield a metalcontaining ash upon combustion. Many types of ashless dispersants are known in the prior art, and any of these is suitable for use in the present invention. The ashless dispersants which can be utilized in the present invention include the following: carboxylic dispersants; amine dispersants; Mannich dispersants; polymeric dispersants; and carboxylic, amine or Mannich dispersants post-treated with such reagents as urea, thiourea, carbon disulfide, aldehydes, ketones, carboxylic acids, hydrocarbon-substituted succinic anhydrides, nitriles, epoxides, boron compounds, phosphorus compounds, etc.

The amine dispersants are reaction products of relatively high molecular weight aliphatic or alicyclic halides with amines, preferably polyalkylene polyamines. Amine dispersants are known and have been described in the prior art such as in U.S. Pat. Nos. 3,275,554; 3,438,757; 3,454,555; and 3,565,804. Mannich dispersants are reaction products of alkyl phenols in which the alkyl group contains at least about 30 carbon atoms with aldehydes (especially formaldehyde) and amines (especially polyalkylene polyamines). The materials described in the following patents are illustrative of Mannich dispersants: U.S. Pat. Nos. 3,413,347; 3,697,574; 3,725,277; 3,725,480; 3,726,882; and 4,454,059.

Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like are useful ashless dispersants. Exemplary materials of this kind are described in the following U.S. Pat. Nos. 3,036,003; 3,200,107; 3,254,025; 3,278,550; 3,281,428; 3,282,955; 3,366,569; 3,373,111; 3,442,808; 3,455,832; 3,493,520; 3,513,093; 3,539,633; 3,579,450; 3,600,372; 3,639,242; 3,649,659; 3,703,536; and 3,708,522. Polymeric dispersants are interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. Polymeric dispersants are disclosed in the following U.S. Pat. Nos. 3,329,658; 3,449,250; 3,519,565; 3,666,730; 3,687,849; and 3,702,300. All of the above-noted patents are incorporated by reference herein for their disclosures of ashless dispersants.

The carboxylic dispersants generally are reaction products of substituted carboxylic acylating agents such as substituted carboxylic acids or derivatives thereof with (a) amines characterized by the presence within their structure of at least one >NH group, (b) organic hydroxy compounds such as hydroxy aromatic compounds and alcohols, (c) basic inorganic materials such as reactive metal or reactive metal compounds, and (d) mixtures of two or more of (a) through (c). The dispersants which are obtained by the reaction of a substituted carboxylic acylating agent with an amine compound often are referred to as "acylated amine dispersants" or "carboxylic imide dispersants" such as succinimide dispersants. The ashless dispersants obtained by the reaction of a substituted carboxylic acylating agent with an alcohol or phenol generally are referred to as carboxylic ester dispersants.

The substituted carboxylic acylating agent may be derived from a monocarboxylic acid or a polycarboxylic acid. Polycarboxylic acids generally are preferred. The acylating agents may be a carboxylic acid or derivatives of the carboxylic acid such as the halides, esters, anhydrides, etc. The free carboxylic acids or the anhydrides of polycarboxylic acids are preferred acylating agents.

In one embodiment, the ashless dispersants utilized in the present invention are the acylated amines or dispersants obtained by reaction of a carboxylic acylating agent with at least one amine containing at least one hydrogen attached to a nitrogen group. In one preferred embodiment, the acylating agent is a hydrocarbon-substituted succinic acid acylating agent.

The nitrogen-containing carboxylic dispersants useful in the present invention are known in the art and have been described in many U.S. Pat. Nos. including 3,172,892 3,341,542 3,630,904 3,215,707 3,444,170 3,632,511 3,219,666 3,454,607 3,787,374 3,316,177 3,541,012 4,234,435 The above U.S. patents are expressly incorporated herein by reference for their teaching of the preparation of nitrogen-containing carboxylic dispersants.

In general, the nitrogen-containing carboxylic dispersants are produced by reacting at least one substituted succinic acylating agent with at least one amine compound containing at least one >HN group, and wherein said acylating agent consists of substituent groups and succinic groups wherein the substituent groups are derived from a polyalkene characterized by an Mn value (number average molecular weight) of at least about 700, and more generally from about 700 to about 5000. Generally, the reaction involves from about 0.5 equivalent to about 2 moles of the amine compound per equivalent of acylating agent.

Similarly, the carboxylic ester dispersants are prepared by reacting the carboxylic acylating agents described above with one or more alcohols or hydroxy aromatic compounds in ratios of from about 0.5 equivalent to about 2 moles of hydroxy compound per equivalent of acylating agent. The preparation of carboxylic ester dispersant is described in the prior art such as U.S. Pat. 3,522,179 and 4,234,435.

Preferred ashless dispersants for use in the present invention are carboxylic esters produced by reacting (A-2-b-1) at least one substituted succinic acylating agent with (A-2-b-2) at least one alcohol or aromatic hydroxy compounds of the general formula $$R_1(OH)_m \qquad (I)$$

wherein $R_1$ is a monovalent or polyvalent organic group joined to the —OH groups through carbon bonds, and m is an integer of from 1 to about 10. The carboxylic esters are included in the oil solutions (A-2) to provide dispersancy.

The substituted succinic acylating agent (A-2-b-1) utilized in the preparation of the carboxylic esters can be characterized by the presence within its structure of two groups or moieties. The first group or moiety is referred to hereinafter, for convenience, as the "substituent group(s)" and is derived from a polyalkene.

The polyalkene from which the substituent is derived is characterized as containing at least about 8 carbon atoms, and, more often, at least about 30 carbon atoms. In one embodiment the polyalkene has a number average molecular weight of at least about 700. Number average molecular weights of from about 700 to about 5000 are preferred. In another preferred embodiment, the substituent groups of the acylating agent are derived from polyalkenes which are characterized by an $\overline{M}n$ value of about 1300 to 5000 and an $\overline{M}w/\overline{M}n$ value of about 1.5 to about 4.5. The term $\overline{M}w$ refers to weight average molecular weight.

The second group or moiety in the acylating agent is referred to herein as the "succinic group(s)". The succinic groups are those groups characterized by the structure

wherein X and X' are the same or different provided at least one of X and X' is such that the substituted succinic acylating agent can function as carboxylic acylating agents. That is, at least one of X and X' must be such that the substituted acylating agent can form amides or amine salts with amino compounds, and otherwise function as a conventional carboxylic acid acylating agents. Transamidation reactions are considered, for purposes of this invention, as conventional acylating reactions.

Thus, X and/or X' is usually —OH, —O—hydrocarbyl, —O—M⁺ where M⁺ represents one equivalent of a metal, ammonium or amine cation, —NH₂, —Cl, —Br, and together, X and X' can be —O—so as to form the anhydride. The specific identity of any X or X' group which is not one of the above is not critical so long as its presence does not prevent the remaining group from entering into acylation reactions. Preferably, however, X and X' are each such that both carboxyl functions of the succinic group (i.e., both —C(O)X and —C(O)X' can enter into acylation reactions.

One of the unsatisfied valences in the grouping

of Formula II forms a carbon-to-carbon bond with a carbon atom in the substituent group. While other such unsatisfied valence may be satisfied by a similar bond with the same or different substituent group, all but the said one such valence is usually satisfied by hydrogen; i.e., —H.

Polyalkenes having the Mn and Mw values discussed above are known in the art and can be prepared according to conventional procedures. For example, some of these polyalkenes are described and exemplified in U.S. Pat. No. 4,234,435, and the disclosure of this patent relative to such polyalkenes is hereby incorporated by reference. Several such polyalkenes, especially polybutenes, are commercially available.

In one preferred embodiment, the succinic groups will normally correspond to the formula

wherein R and R' are each independently selected from the group consisting of —OH, —Cl, —O—lower alkyl, and when taken together, R and R' are —O—. In the latter case, the succinic group is a succinic anhydride group. All the succinic groups in a particular succinic acylating agent need not be the same, but they can be the same. Preferably, the succinic groups will correspond to

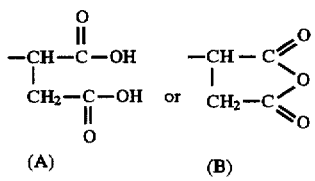

and mixtures of (IV(A)) and (IV(B)).

The polyalkenes from which the substituent groups are derived are homopolymers and interpolymers of polymerizable olefin monomers of 2 to about 16 carbon atoms; usually 2 to about 6 carbon atoms. The interpolymers are those in which two or more olefin monomers are interpolymerized according to well-known conventional procedures to form polyalkenes having units within their structure derived from each of said two or more olefin monomers. Thus, "interpolymer(s)" as used herein is inclusive of copolymers, terpolymers, tetrapolymers, and the like. As will be apparent to those of ordinary skill in the art, the polyalkenes from which the substituent groups are derived are often conventionally referred to as "polyolefin(s)".

The olefin monomers from which the polyalkenes are derived are polymerizable olefin monomers characterized by the presence of one or more ethylenically unsaturated groups (i.e., >C=C<); that is, they are monoolefinic monomers such as ethylene, propylene, butene-1, isobutene, and octene-1 or polyolefinic monomers (usually diolefinic monomers) such as butadiene-1,3 and isoprene.

These olefin monomers are usually polymerizable terminal olefins; that is, olefins characterized by the presence in their structure of the group >C=CH$_2$. However, polymerizable internal olefin monomers (sometimes referred to in the literature as medial olefins) characterized by the presence within their structure of the group

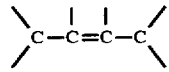

can also be used to form the polyalkenes. When internal olefin monomers are employed, they normally will be employed with terminal olefins to produce polyalkenes which are interpolymers. For purposes of this invention, when a particular polymerized olefin monomer can be classified as both a terminal olefin and an internal olefin, it will be deemed to be a terminal olefin. Thus, pentadiene-1,3 (i.e., piperylene) is deemed to be a terminal olefin for purposes of this invention.

While the polyalkenes from which the substituent groups of the succinic acylating agents are derived generally are hydrocarbon groups, they can contain nonhydrocarbon substituents such as lower alkoxy, lower alkyl mercapto, hydroxy, mercapto, nitro, halo, cyano, carboalkoxy, (where alkoxy is usually lower alkoxy), alkanoyloxy, and the like provided the non-hydrocarbon substituents do not substantially interfere with formation of the substituted succinic acid acylating agents of this invention. When present, such non-hydrocarbon groups normally will not contribute more than about 10% by weight of the total weight of the polyalkenes. Since the polyalkene can contain such non-hydrocarbon substituents, it is apparent that the olefin monomers from which the polyalkenes are made can also contain such substituents. Normally, however, as a matter of practicality and expense, the olefin monomers and the polyalkenes will be free from non-hydrocarbon groups, except chloro groups which usually facilitate the formation of the substituted succinic acylating agents of this invention. (As used herein, the term "lower" when used with a chemical group such as in "lower alkyl" or "lower alkoxy" is intended to describe groups having up to 7 carbon atoms).

Although the polyalkenes may include aromatic groups (especially phenyl groups and lower alkyl- and/or lower alkoxy-substituted phenyl groups such as para-(tert-butyl)phenyl) and cycloaliphatic groups such as would be obtained from polymerizable cyclic olefins or cycloaliphatic substituted-polymerizable acyclic olefins, the polyalkenes usually will be free from such groups. Nevertheless, polyalkenes derived from interpolymers of both 1,3-dienes and styrenes such as butadiene-1,3 and styrene or para-(tert-butyl)styrene are exceptions to this generalization. Again, because aromatic and cycloaliphatic groups can be present, the olefin monomers from which the polyalkenes are prepared can contain aromatic and cycloaliphatic groups.

There is a general preference for aliphatic, hydrocarbon polyalkenes free from aromatic and cycloaliphatic groups. Within this general preference, there is a further preference for polyalkenes which are derived from the group consisting of homopolymers and interpolymers of terminal hydrocarbon olefins of 2 to about 16 carbon atoms. This further preference is qualified by the proviso that, while interpolymers of terminal olefins are usually preferred, interpolymers optionally containing up to about 40% of polymer units derived from internal olefins of up to about 16 carbon atoms are also within a preferred group. A more preferred class of polyalkenes are those selected from the group consisting of homopolymers and interpolymers of terminal olefins of 2 to about 6 carbon atoms, more preferably 2 to 4 carbon atoms. However, another preferred class of polyalkenes are the latter more preferred polyalkenes optionally containing up to about 25% of polymer units derived from internal olefins of up to about 6 carbon atoms.

Specific examples of terminal and internal olefin monomers which can be used to prepare the polyalkenes according to conventional, well-known polymerization techniques include ethylene; propylene; butene-1; butene-2; isobutene; pentene-1; hexene-1; heptene-1; octene-1; nonene-1; decene-1; pentene-2; propylene-tetramer; diisobutylene; isobutylene trimer; butadiene-1,2; butadiene-1,3pentadiene-1,2; pentadiene-1,3; pentadiene-1,4; isoprene; hexadiene-1, 5; 2-chloro-butadiene 1,3; 2-methyl-heptene- 1; 3-cyclohexylbutene-1; 2-methyl-pentene-1; styrene; 2,4-dichloro styrene; divinylbenzene; vinyl acetate; allyl alcohol; 1-methyl-vinylacetate acrylonitrile; ethyl acrylate; methyl methacrylate; ethyl vinyl ether; and methyl vinyl ketone. Of these, the hydrocarbon polymerizable monomers are preferred and of these hydrocarbon monomers, the terminal olefin monomers are particularly preferred.

Specific examples of polyalkenes include polypropylenes, polybutenes, ethylene-propylene copolymers, styrene-isobutene copolymers, isobutene-butadiene-1,3 copolymers, propene-isoprene copolymers, isobutene-chloroprene copolymers, isobutene-(paramethyl)styrene copolymers, copolymers of hexene-1with hexadiene-1,3, copolymers of octene-1with hexene-1, copolymers of heptene-1with pentene-1, copolymers of 3-methyl-butene-1 with octene-1, copolymers of 3,3-dimethyl-pentene-1 with hexene-1, and terpolymers of isobutene, styrene and piperylene. More specific examples of such interpolymers include copolymer of 95% (by weight) of isobutene with 5% (by weight) of styrene; terpolymer of 98% of isobutene with 1% of piperylene and 1% of chloroprene; terpolymer of 95% of isobutene with 2% of butene-1and 3% of hexene-1; terpolymer of 60% of isobutene with 20% of pentene-1and 20% of octene-1; copolymer of 80% of hexene-1and 20% of heptene-1; terpolymer of 90% of isobutene with 2% of cyclohexene and 8% of propylene; and copolymer of 80% of ethylene and 20% of propylene. A preferred source of polyalkenes are the poly(isobutene)s obtained by polymerization of $C_4$ refinery stream having a butene content of about 35 to about 75% by weight and an isobutene content of about 30 to about 60% by weight in the presence of a Lewis acid catalyst such as aluminum trichloride or boron trifluoride. These polybutenes contain predominantly (greater than about 80% of the total repeating units) of isobutene (isobutylene) repeating units of the configuration

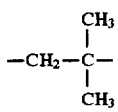

The polyalkene from which the substituted groups are derived may be characterized by an $\overline{Mn}$ value of from about 1300 to about 5000, and an $\overline{Mw}/\overline{Mn}$ value of at least about 1.5 and more generally from about 1.5 to about 4.5 or about 1.5 to about 4.0. The abbreviation Mw is the conventional symbol representing weight average molecular weight, and Mn is the conventional symbol representing number average molecular weight. Gel permeation chromatography (GPC) is a method which provides both weight average and number average molecular weights as well as the entire molecular weight distribution of the polymers. For purpose of this invention a series of fractionated polymers of isobutene, polyisobutene, is used as the calibration standard in the GPC.

The techniques for determining Mn and Mw values of polymers are well known and are described in numerous books and articles. For example, methods for the determination of Mn and molecular weight distribution of polymers is described in W. W. Yan, J. J. Kirkland and D. D. Bly, "Modern Size Exclusion Liquid Chromatographs", J.Wiley & Sons, Inc., 1979.

Obviously, preparing polyalkenes as described above which meet the various criteria for $\overline{Mn}$ and $\overline{Mw}/\overline{Mn}$ is within the skill of the art and does not comprise part of the present invention. Techniques readily apparent to those in the art include controlling polymerization temperatures, regulating the amount and type of polymerization initiator and/or catalyst, employing chain terminating groups in the polymerization procedure, and the like. Other conventional techniques such as stripping (including vacuum stripping) a very light end and/or oxidatively or mechanically degrading high molecular weight polyalkene to produce lower molecular weight polyalkenes can also be used.

In preparing the substituted succinic acylating agents (A-2-b-1), one or more of the above-described polyalkenes is reacted with one or more acidic reactants selected from the group consisting of maleic or fumaric reactants of the general formula

wherein X and X' are as defined hereinbefore in Formula II. Preferably the maleic and fumaric reactants will be one or more compounds corresponding to the formula

wherein R and R' are as previously defined in Formula III herein. Ordinarily, the maleic or fumaric reactants will be maleic acid, fumaric acid, maleic anhydride, or a mixture of two or more of these. The maleic reactants are usually preferred over the fumaric reactants because the former are more readily available and are, in general, more readily reacted with the polyalkenes (or derivatives thereof) to prepare the substituted succinic acylating agents of the present invention. The especially preferred reactants are maleic acid, maleic anhydride, and mixtures of these. Due to availability and ease of reaction, maleic anhydride will usually be employed.

The one or more polyalkenes and one or more maleic or fumaric reactants can be reacted according to any of several known procedures in order to produce the substituted succinic acylating agents useful in the present invention. For convenience and brevity, the term "maleic reactant" is often used hereinafter. When used, it should be understood that the term is generic to acidic reactants selected from maleic and fumaric reactants corresponding to Formulae (V) and (VI) above including a mixture of such reactants.

One procedure for preparing the substituted succinic acylating agents (A-2-b-1) is illustrated, in part, in U.S. Pat. No. 3,219,666 (Norman et al) which is expressly incorporated herein by reference for its teachings in regard to preparing succinic acylating agents. This procedure is conveniently designated as the "two-step procedure". It involves first chlorinating the polyalkene until there is an average of at least about one chloro group for each molecular weight of polyalkene. (For purposes of this invention, the molecular weight of the polyalkene is the weight corresponding to the $\overline{Mn}$ value.) Chlorination involves merely contacting the polyalkene with chlorine gas until the desired amount of chlorine is incorporated into the chlorinated polyalkene. Chlorination is generally carried out at a temperature of about 75° C. to about 125° C. If a diluent is used in the chlorination procedure, it should be one which is not itself readily subject to further chlorination. Poly- and perchlorinated and/or fluorinated alkanes and benzenes are examples of suitable diluents.

The second step in the two-step chlorination procedure is to react the chlorinated polyalkene with the maleic reactant at a temperature usually within the range of about 100° C. to about 200° C. The mole ratio of chlorinated polyalkene to maleic reactant is usually at least about 1:1.3. (In this application, a mole of chlorinated polyalkene is that weight of chlorinated polyalkene corresponding to the $\overline{Mn}$ value of the unchlorinated polyalkene.) However, a stoichiometric excess of maleic reactant can be used, for example, a mole ratio of 1:2. More than one mole of maleic reactant may react per molecule of chlorinated polyalkene. Because of such situations, it is better to describe the ratio of chlorinated polyalkene to maleic reactant in terms of equivalents. (An equivalent weight of chlorinated polyalkene, for purposes of this invention, is the weight corresponding to the $\overline{Mn}$ value divided by the average number of chloro groups per molecule of chlorinated polyalkene while the equivalent weight of a maleic reactant is its molecular weight.) Thus, the ratio of chlorinated polyalkene to maleic reactant will normally be such as to provide at least about 1.3 equivalents of maleic reactant for each mole of chlorinated polyalkene. Unreacted excess maleic reactant may be stripped from the reaction product, usually under vacuum, or reacted during a further stage of the process as explained below.

The resulting polyalkenyl-substituted succinic acylating agent is, optionally, again chlorinated if the desired number of succinic groups are not present in the product. If there is present, at the time of this subsequent chlorination, any excess maleic reactant from the second step, the excess will react as additional chlorine is introduced during the subsequent chlorination. Otherwise, additional maleic reactant is introduced during and/or subsequent to the additional chlorination step. This technique can be repeated until the total number of succinic groups per equivalent weight of substituent groups reaches the desired level.

Another procedure for preparing the substituted succinic acid acylating agents (A-2-b-1) utilizes a process described in U.S. Pat. No. 3,912,764 (Palmer) and U.K. Patent 1,440, 219, both of which are expressly incorporated herein by reference for their teachings in regard to that process. According to that process, the polyalkene and the maleic reactant are first reacted by heating them together in a "direct alkylation" procedure. When the direct alkylation step is completed, chlorine is introduced into the reaction mixture to promote reaction of the remaining unreacted maleic reactants. According to the patents, 0.3 to 2 or more moles of maleic anhydride are used in the reaction for each mole of olefin polymer; i.e., polyalkene. The direct alkylation step is conducted at temperatures of 180° C. to 250° C. During the chlorine-introducing stage, a temperature of 160° C. to 225° C. is employed. In utilizing this process to prepare the substituted succinic acylating agents, it is necessary to use sufficient maleic reactant and chlorine to incorporate at least 1.3 succinic groups into the final product, i.e., the substituted succinic acylating agent, for each equivalent weight of polyalkene, i.e., reacted polyalkenyl in final product.

Other processes for preparing the acylating agents (A-2-b-1) are also described in the prior art. U.S. Pat. No. 4,110,349 (Cohen) describes a two-step process and the disclosure of U.S. Pat. No. 4,110,349 relating to the two-step process for preparing-acylating agent is hereby incorporated by reference.

One preferred process for preparing the substituted succinic acylating agents (A-2-b-1) from the standpoint of efficiency, overall economy, and the performance of the acylating agents thus produced, as well as the performance of the derivatives thereof, is the so called "one-step" process. This process is described in U.S. Pat. Nos. 3,215,707 (Rense) and 3,231,587 (Rense). Both are expressly incorporated herein by reference for their teachings in regard to that process.

Basically, the one-step process involves preparing a mixture of the polyalkene and the maleic reactant containing the necessary amounts of both to provide the desired substituted succinic acylating agents. This means that there must be at least 1.3 moles of maleic reactant for each mole of polyalkene in order that there can be at least 1.3 succinic groups for each equivalent weight of substituent groups. Chlorine is then introduced into the mixture, usually by passing chlorine gas through the mixture with agitation, while maintaining a temperature of at least about 140° C.

A variation on this process involves adding additional maleic reactant during or subsequent to the chlorine introduction but, for reasons explained in U.S. Pat. Nos. 3,215, 707 and 3,231,587, this variation is presently not as preferred as the situation where all the polyalkene and all the maleic reactant are first mixed before the introduction of chlorine.

Usually, where the polyalkene is sufficiently fluid at 140° C. and above, there is no need to utilize an additional substantially inert, normally liquid solvent/diluent in the one-step process. However, as explained hereinbefore, if a solvent/diluent is employed, it is preferably one that resists chlorination. Again, the poly- and per-chlorinated and/or -fluorinated alkanes, cycloalkanes, and benzenes can be used for this purpose.

Chlorine may be introduced continuously or intermittently during the one-step process. The rate of introduction of the chlorine is not critical although, for maximum utilization of the chlorine, the rate should be about the same as the rate of consumption of chlorine in the course of the reaction. When the introduction rate of chlorine exceeds the rate of consumption, chlorine is evolved from the reaction mixture. It is often advantageous to use a closed system, including superatmospheric pressure, in order to prevent loss of chlorine and maleic reactant so as to maximize reactant utilization.

The minimum temperature at which the reaction in the one-step process takes place at a reasonable rate is about 140° C. Thus, the minimum temperature at which the process is normally carried out is in the neighborhood of 140° C. The preferred temperature range is usually between about 160° C. and about 220° C. Higher temperatures such as 250° C. or even higher may be used but usually with little advantage. In fact, temperatures in excess of 220° C. are often disadvantageous with respect to preparing the particular acylated succinic compositions of this invention because they tend to "crack" the polyalkenes (that is, reduce their molecular weight by thermal degradation) and/or decompose the maleic reactant. For this reason, maximum temperatures of about 200° C. to about 210° C. are normally not exceeded. The upper limit of the useful temperature in the one-step process is determined primarily by the decomposition point of the components in the reaction mixture including the reactants and the desired products. The decomposition point is that temperature at which there is sufficient decomposition of any reactant or product such as to interfere with the production of the desired products.

In the one-step process, the molar ratio of maleic reactant to chlorine is such that there is at least about one mole of chlorine for each mole of maleic reactant to be incorporated into the product. Moreover, for practical reasons, a slight excess, usually in the neighborhood of about 5% to about 30% by weight of chlorine, is utilized in order to offset any loss of chlorine from the reaction mixture. Larger amounts of excess chlorine may be used but do not appear to produce any beneficial results.

As mentioned previously, in one embodiment, the molar ratio of polyalkene to maleic reactant is such that there are at least about 1.3 moles of maleic reactant for each mole of polyalkene. This is necessary in order that there can be at least 1.3 succinic groups per equivalent weight of substituent group in the product. Preferably, however, an excess of maleic reactant is used. Thus, ordinarily about a 5% to about 25% excess of maleic reactant will be used relative to that amount necessary to provide the desired number of succinic groups in the product.

The terminology "substituted succinic acylating agent(s)" is used herein in describing the substituted succinic acylating agents regardless of the process by which they are produced. Obviously, as discussed in more detail hereinbefore, several processes are available for producing the substituted succinic acylating agents. On the other hand, the terminology "substituted acylating composition(s)", may be used to describe the reaction mixtures produced by the specific preferred processes described in detail herein. Thus, the identity of particular substituted acylating compositions is dependent upon a particular process of manufacture. This is particularly true because, while the products of this invention are clearly substituted succinic acylating agents as defined and discussed above, their structure cannot be represented by a single specific chemical formula. In fact, mixtures of products are inherently present. For purposes of brevity, the terminology "acylating reagent(s)" is often used hereafter to refer, collectively, to both the substituted succinic acylating agents and to the substituted acylating compositions used in this invention.

The carboxylic esters (A-2-b) are those of the above-described succinic acylating agents with hydroxy compounds [R₁(OH)m] as defined earlier with respect to Formula I which may be aliphatic compounds such as monohydric and polyhydric alcohols or aromatic hydroxy compounds such as phenols and naphthols.

Aromatic hydroxy compounds include phenols (which are preferred), carbon-, oxygen-, sulfur- and nitrogen-bridged phenols and the like as well as phenols directly linked through covalent bonds (e.g., 4,4'-bis-(hydroxy)biphenyl, hydroxy compounds derived from fused-ring hydrocarbon (e.g., naphthols and the like); and polyhydroxy compounds such as catechol, resorcinol and hydroquinone. Mixtures of one or more aromatic hydroxy compounds can be used as the first reagent.

These aromatic hydroxy compounds are preferably substituted with at least one, and preferably not more than two, aliphatic or alicyclic substituents having at least about 6 (usually at least about 30, more preferably at least 50) carbon atoms and up to about 7000 carbon atoms. Examples of such substituents derived from the polymerization of olefins such as ethylene, propylene, 1-butene, 2-butene, isobutene and the like. Both homopolymers (made from a single olefin monomer) and interpolymers (made from two or more of olefin monomers) can serve as sources of these substituents and are encompassed in the term "polymers" as used herein. Substituents derived from polymers of ethylene, propylene, 1-butene and isobutene are preferred, especially those containing at least about 30 and preferably at least about 50 aliphatic carbon atoms.

Introduction of the aliphatic or alicyclic substituent onto the phenol or other aromatic hydroxy compound is usually effected by mixing a hydrocarbon (or a halogenated derivative thereof, or the like) and the phenol at a temperature of about 50°–200° C. in the presence of a suitable catalyst, such as aluminum trichloride, boron trifluoride, zinc chloride or the like. See, for example, U.S. Pat. No. 3,368,972 which is incorporated by reference for its disclosures in this regard. This substituent can also be introduced by other alkylation processes known in the art.

The aromatic hydroxy compounds from which the esters may be derived are illustrated by the following specific examples: phenol, beta-naphthol, alpha-naphthol, cresol, resorcinol, catechol, p,p'-dihydroxybiphenyl, 2-chlorophenol, 2,4-dibutylphenol, etc.

The alcohols from which the esters may be derived preferably contain up to about 40 aliphatic carbon atoms. They may be monohydric alcohols such as methanol, ethanol, isooctanol, dodecanol, cyclohexanol, cyclopentanol, behenyl alcohol, hexatriacontanol, neopentyl alcohol, isobutyl alcohol, benzyl alcohol, beta-phenylethyl alcohol, 2-methylcyclohexanol, beta-chloroethanol, monomethyl ether of ethylene glycol, monobutyl ether of ethylene glycol, monopropyl ether of diethylene glycol, monododecyl ether of triethylene glycol, mono-oleate of ethylene glycol, monostearate of diethylene glycol, secpentyl alcohol, tert-butyl alcohol, 5-bromo-dodecanol, nitrooctadecanol and dioleate of glycerol. The polyhydric alcohols preferably contain from 2 to about 10 hydroxy groups. They are illustrated by, for example, ethylene glycol, diethylene glycol, triethylene glycol, tetraethylene glycol, dipropylene glycol, tripropylene glycol, dibutylene glycol, tributylene glycol, and other alkylene glycols in which the alkylene group contains from 2 to about 8 carbon atoms. Other useful polyhydric alcohols include glycerol, monooleate of glycerol, monostearate of glycerol, monomethyl ether of glycerol, pentaerythritol, 9,10-dihydroxy stearic acid, 1,2-butanediol, 2,3-hexanediol, 2,4-hexanediol, pinacol, erythritol, arabitol, sorbitol, mannitol, 1,2-cyclo-hexanediol, and xylylene glycol.

An especially preferred class of polyhydric alcohols are those having at least three hydroxy groups, some of which have been esterified with a monocarboxylic acid having from about 8 to about 30 carbon atoms such as octanoic acid, oleic acid, stearic acid, linoleic acid, dodecanoic acid, or tall oil acid. Examples of such partially esterified polyhydric alcohols are the monooleate of sorbitol, distearate of sorbitol, monooleate of glycerol, monostearate of glycerol, di-dodecanoate of erythritol.

The esters (A-2-b) may also be derived from unsaturated alcohols such as allyl alcohol, cinnamyl alcohol, propargyl alcohol, 1-cyclohexen-3-ol, and oleyl alcohol. Still other classes of the alcohols capable of yielding the esters of this invention comprises the ether-alcohols and amino-alcohols including, for example, the oxy-alkylene-, oxy-arylene-, amino-alkylene-, and amino-arylene-substituted alcohols having one or more oxy-alkylene, amino-alkylene or amino-arylene oxy-arylene groups. They are exemplified by Cellosolve, Carbitol, phenoxy-ethanol, mono(heptylphenyloxypropylene) -substituted glycerol, poly' styrene oxide), amino-ethanol, 3-amino ethylpentanol, di(hydroxyethyl) amine, p-aminophenol, tri(hydroxypropyl)amine, N-hydroxyethyl ethylene diamine, N,N,N',N'-tetrahydroxytrimethylene diamine, and the like. For the most part, the ether-alcohols having up to about 150 oxy-alkylene groups in which the alkylene group contains from 1 to about 8 carbon atoms are preferred.

The esters may be diesters of succinic acids or acidic esters, i.e., partially esterified succinic acids; as well as partially esterified polyhydric alcohols or phenols, i.e., esters having free alcoholic or phenolic hydroxyl groups. Mixtures of the above-illustrated esters likewise are contemplated within the scope of this invention.

A suitable class of esters for use in this invention are those diesters of succinic acid and an alcohol having up to about 9 aliphatic carbon atoms and having at least one substituent selected from the class consisting of amino and carboxy groups wherein the hydrocarbon substituent of the succinic acid is a polymerized butene substituent having a number average molecular weight of from about 700 to about 5000.

The esters (A-2-b) may be prepared by one of several known methods. The method which is preferred because of convenience and the superior properties of the esters it produces, involves the reaction of a suitable alcohol or phenol with a substantially hydrocarbon-substituted succinic anhydride. The esterification is usually carried out at a temperature above about 100° C., preferably between 150° C. and 300° C. The water formed as a by-product is removed by distillation as the esterification proceeds.

In most cases the carboxylic esters are a mixture of esters, the precise chemical composition and the relative proportions of which in the product are difficult to determine. Consequently, the product of such reaction is best described in terms of the process by which it is formed.

A modification of the above process involves the replacement of the substituted succinic anhydride with the corresponding succinic acid. However, succinic acids readily undergo dehydration at temperatures above about 100° C. and are thus converted to their anhydrides which are then esterified by the reaction with the alcohol reactant. In this regard, succinic acids appear to be the substantial equivalent of their anhydrides in the process.

The relative proportions of the succinic reactant and the hydroxy reactant which are to be used depend to a large measure upon the type of the product desired and the number of hydroxyl groups present in the molecule of the hydroxy reactant. For instance, the formation of a half ester of a succinic acid, i.e., one in which only one of the two acid groups is esterified, involves the use of one mole of a monohydric alcohol for each mole of the substituted succinic acid reactant, whereas the formation of a diester of a succinic acid involves the use of two moles of the alcohol for each mole of the acid. On the other hand, one mole of a hexahydric alcohol may combine with as many as six moles of a succinic acid to form an ester in which each of the six hydroxyl groups of the alcohol is esterified with one of the two acid groups of the succinic acid. Thus, the maximum proportion of the succinic acid to be used with a polyhydric alcohol is determined by the number of hydroxyl groups present in the molecule of the hydroxy reactant. In one embodiment, esters obtained by the reaction of equimolar amounts of the succinic acid reactant and hydroxy reactant are preferred.

In some instances it is advantageous to carry out the esterification in the presence of a catalyst such as sulfuric acid, pyridine hydrochloride, hydrochloric acid, benzene sulfonic acid, p-toluene sulfonic acid, phosphoric acid, or any other known esterification catalyst. The amount of the catalyst in the reaction may be as little as 0.01% (by weight of the reaction mixture), more often from about 0.1% to about 5%.

The esters (A-2-b) may be obtained by the reaction of a substituted succinic acid or anhydride with an epoxide or a mixture of an epoxide and water. Such reaction is similar to one involving the acid or anhydride with a glycol. For instance, the ester may be prepared by the reaction of a substituted succinic acid with one mole of ethylene oxide. Similarly, the ester may be obtained by the reaction of a substituted succinic acid with two moles of ethylene oxide. Other epoxides which are commonly available for use in such reaction include, for example, propylene oxide, styrene oxide, 1,2-butylene oxide, 2,3-butylene oxide, epichlorohydrin, cyclohexene oxide, 1,2-octylene oxide, epoxidized soybean oil, methyl ester of 9,10-epoxy-stearic acid, and butadiene mono-epoxide. For the most part, the epoxides are the alkylene oxides in which the alkylene group has from 2 to about 8 carbon atoms; or the epoxidized fatty acid esters in which the fatty acid group has up to about 30 carbon atoms and the ester group is derived from a lower alcohol having up to about 8 carbon atoms.

In lieu of the succinic acid or anhydride, a substituted succinic acid halide may be used in the processes illustrated above for preparing the esters. Such acid halides may be acid dibromides, acid dichlorides, acid monochlorides, and acid monobromides. The substituted succinic anhydrides and acids can be prepared by, for example, the reaction of maleic anhydride with a high molecular weight olefin or a halogenated hydrocarbon such as is obtained by the chlorination of an olefin polymer described previously. The reaction involves merely heating the reactants at a temperature preferably from about 100° C. to about 250° C. The product from such a reaction is an alkenyl succinic anhydride. The alkenyl group may be hydrogenated to an alkyl group. The anhydride may be hydrolyzed by treatment with water or steam to the corresponding acid. Another method useful for preparing the succinic acids or anhydrides involves the reaction of itaconic acid or anhydride with an olefin or a chlorinated hydrocarbon at a temperature usually within the range from about 100° C. to about 250° C. The succinic acid halides can be prepared by the reaction of the acids or their anhydrides with a halogenation agent such as phosphorus tribromide, phosphorus pentachloride, or thionyl chloride. These and other methods of preparing the carboxylic esters (A-2-b) are well known in the art and need not be illustrated in further detail here. For example, see U.S. Pat. No. 3,522,179 which is hereby incorporated by reference for its disclosure of the preparation of carboxylic ester compositions useful as component (A-2-b).

The preparation of carboxylic ester derivative compositions from acylating agents wherein the substituent groups are derived from polyalkenes characterized by an $\overline{M}n$ of at least about 1300 up to about 5000 and an $\overline{M}w/\overline{M}n$ ratio of from 1.5 to about 4 is described in U.S. Pat. No. 4,234,435 which is hereby incorporated by reference. The acylating agents described in the '435 patent are also characterized as having within their structure an average of at least 1.3 succinic groups for each equivalent weight of substituent groups.

The following examples illustrate the esters (A-2-b) and the processes for preparing such esters.

EXAMPLE E-1

A substantially hydrocarbon-substituted succinic anhydride is prepared by chlorinating a polyisobutene having a number average molecular weight of 1000 to a chlorine content of 4.5% and then heating the chlorinated polyisobutene with 1.2 molar proportions of maleic anhydride at a temperature of 150°–220° C. A mixture of 874 grams (1 mole) of the succinic anhydride and 104 grams (1 mole) of neopentyl glycol is maintained at 240°–250° C./30 mm for 12 hours. The residue is a mixture of the esters resulting from the esterification of one and both hydroxy groups of the glycol.

EXAMPLE E-2

The dimethyl ester of the substantially hydrocarbon-substituted succinic anhydride of Example E-1 is prepared by heating a mixture of 2185 grams of the anhydride, 480 grams of methanol, and 1000 cc of toluene at 50°–65° C. while hydrogen chloride is bubbled through the reaction mixture for 3 hours. The mixture is then heated at 60°–65° C. for 2 hours, dissolved in benzene, washed with water, dried and filtered. The filtrate is heated at 150° C./60 mm to remove volatile components. The residue is the desired dimethyl ester.

EXAMPLE E-3

The substantially hydrocarbon-substituted succinic anhydride of Example E-1 is partially esterified with an ether-alcohol as follows. A mixture of 550 grams (0.63 mole) of the anhydride and 190 grams (0.32 mole) of a commercial polyethylene glycol having a molecular weight of 600 is heated at 240°–250° C. for 8 hours at atmospheric pressure and 12 hours at a pressure of 30 mm. Hg until the acid number of the reaction mixture is reduced to about 28. The residue is the desired acidic ester.

EXAMPLE E-4

A mixture of 926 grams of a polyisobutene-substituted succinic anhydride having an acid number of 121, 1023 grams of mineral oil, and 124 grams (2 moles per mole of the anhydride) of ethylene glycol is heated at 50°–170° C. while hydrogen chloride is bubbled through the reaction mixture for 1.5 hours. The mixture is then heated to 250° C./30 mm and the residue is purified by washing with aqueous sodium hydroxide followed by washing with water, then dried and filtered. The filtrate is a 50% oil solution of the desired ester.

EXAMPLE E-5

A mixture of 438 grams of the polyisobutene-substituted succinic anhydride prepared as is described in Example E-1 and 333 grams of a commercial polybutylene glycol having a molecular weight of 1000 is heated for 10 hours at 150°–160° C. The residue is the desired ester.

EXAMPLE E-6

A mixture of 645 grams of the substantially hydrocarbon-substituted succinic anhydride prepared as is described in Example E-1 and 44 grams of tetramethylene glycol is heated at 100°–130° C. for 2 hours. To this mixture there is added 51 grams of acetic anhydride (esterification catalyst) and the resulting mixture is heated under reflux at 130°–160° C. for 2.5 hours. Thereafter the volatile components of the mixture are distilled by heating the mixture to 196°–270° C./30 mm and then at 240° C./0.15 mm for 10 hours. The residue is the desired acidic ester.

EXAMPLE E-7

A mixture of 456 grams of a polyisobutene-substituted succinic anhydride prepared as is described in Example E-1 and 350 grams (0.35 mole) of the monophenyl ether of a polyethylene glycol having a molecular weight of 1000 is heated at 150°–155° C. for 2 hours. The product is the desired ester.

EXAMPLE E-8

A dioleyl ester is prepared as follows: a mixture of 1 mole of a polyisobutene-substituted succinic anhydride prepared as in Example E-1, 2 moles of a commercial oleyl alcohol, 305 grams of xylene, and 5 grams of p-toluene sulfonic acid (esterification catalyst) is heated at 150°–173° C. for 4 hours whereupon 18 grams of water is collected as the distillate. The residue is washed with water and the organic layer dried and filtered. The filtrate is heated to 175° C./20 mm and the residue is the desired ester.

EXAMPLE E-9

An ether-alcohol is prepared by the reaction of 9 moles of ethylene oxide with 0.9 mole of a polyisobutene-substituted phenol in which the polyisobutene substituent has a number average molecular weight of 1000. A substantially hydrocarbon-substituted succinic acid ester of this ether-alcohol is prepared by heating a xylene solution of an equimolar mixture of the two reactants in the presence of a catalytic amount of p-toluene sulfonic acid at 157° C.

EXAMPLE E-10

A substantially hydrocarbon-substituted succinic anhydride is prepared as is described in Example E-1 except that a copolymer of 90 weight percent of isobutene and 10 weight percent of piperylene having a number average molecular weight of 66,000 is used in lieu of the polyisobutene. The anhydride has an acid number of about 22. An ester is prepared by heating a toluene solution of an equimolar mixture of the above anhydride and a commercial alkanol consisting substantially of $C_{12-14}$ alcohols at the reflux temperature for 7 hours while water is removed by azeotropic distillation. The residue is heated at 150° C./3 mm to remove volatile components and diluted with mineral oil. A 50% oil solution of the ester is obtained.

EXAMPLE E-11

(A) A mixture of 1000 parts (0.495 mole) of polyisobutene (Mn=2020; Mw=6049) and 115 parts (1.17 moles) of maleic anhydride is heated to 110° C. This mixture is heated to 184° C. in 6 hours during which 85 parts (1.2 moles) of gaseous chlorine is added beneath the surface. At 184°–189° C. an additional 59 parts (0.83 mole) of chlorine is added over 4 hours. The reaction mixture is stripped by heating at 186°–1900° C. with nitrogen blowing for 26 hours. The residue is the desired polyisobutene-substituted succinic acylating agent having a saponification equivalent number of 87 as determined by ASTM procedure D-94.

(B) A mixture of 3225 parts (5.0 equivalents) of the polyisobutene-substituted succinic acylating agent prepared in (A), 289 parts (8.5 equivalents) of pentaerythritol and 5204 parts of mineral oil is heated at 224°–235° C. for 5.5 hours. The reaction mixture is filtered at 130° C. to yield an oil solution of the desired product.

EXAMPLE E-12

A mixture of about 872 grams of mineral oil and 1000 grams of the substituted succinic anhydride prepared as in Example E-1 is heated to about 150°–160° C., and 109 grams of monopentaerythritol are added while maintaining the reaction temperature below about 176° C. The mixture then is heated to about 205° C. and maintained at this temperature for at least 8 hours. The mixture is blown with oxygen for an additional 8 hours at about 205° C. as some water is removed. The mixture is blended with additional oil, if desired, and filtered. The filtrate is an oil solution of the desired ester (45% oil).

The carboxylic esters which are described above resulting from the reaction of an acylating agent with a hydroxy-containing compound such as an alcohol or a phenol may be further reacted with an amine (A-2-b-3), and particularly polyamines.

In one embodiment, the amount of amine (A-2-b-3) which is reacted with the ester is an amount such that there is at least about 0.01 equivalent of the amine for each equivalent of acylating agent initially employed in the reaction with the alcohol. Where the acylating agent has been reacted with the alcohol in an amount such that there is at least one equivalent of alcohol for each equivalent of acylating agent, this small amount of amine is sufficient to react with minor amounts of non-esterified carboxyl groups which may be present. In one preferred embodiment, the amine-modified carboxylic acid esters utilized as component (A-2-b) are prepared by reacting about 1.0 to 2.0 equivalents, preferably about 1.0 to 1.8 equivalents of hydroxy compound, and up to about 0.3 equivalent, preferably about 0.02 to about 0.25 equivalent of polyamine per equivalent of acylating agent.

Acylated nitrogen compositions produced from the acylating reagents (A-2-b-1) and the amines (A-2-b-3) comprise acylated amines which include amine salts, amides, imides, etc., as well as mixtures thereof, which are useful as ashless dispersants of (A-2-b). The acylating reagent and the amine are reacted in amounts sufficient to provide from about one-half equivalent up to about 2 moles of amine per equivalent of acylating reagent. U.S. Pat. Nos. 3,172,892; 3,219,666; 3,272,746; and 4,234,435 are expressly incorporated herein by reference for their disclosures with respect to the procedures applicable to reacting the acylating reagents with the amines as described above.

In another embodiment, the carboxylic acid acylating agent (A-2-b-1) may be reacted simultaneously with both the alcohol and the amine. There is generally at least about 0.01 equivalent of the alcohol and at least 0.01 equivalent of the amine although the total amount of equivalents of the combination should be at least about 0.5 equivalent per equivalent of acylating agent.

The amino compound (A-2-b-3) is characterized by the presence within its structure of at least one HN< group and it can be a monoamine or polyamine compound. Mixtures of two or more amino compounds can be used in the reaction. Preferably, the amino compound contains at least one primary amino group (i.e., —$NH_2$) and more preferably the amine is a polyamine, especially a polyamine containing at least two —NH—groups, either or both of which are primary or secondary amines. The amines may be aliphatic, cycloaliphatic, aromatic, or heterocyclic amines.

The monoamines and polyamines must be characterized by the presence within their structure of at least one HN< group. Therefore, they have at least one primary (i.e., $H_2N$—) or secondary amino (i.e., HN=) group. The amines can be aliphatic, cycloaliphatic, aromatic, or heterocyclic, including aliphatic-substituted cycloaliphatic, aliphatic-substituted aromatic, aliphatic-substituted heterocyclic, cycloaliphatic-substituted aliphatic, cycloaliphatic-substituted heterocyclic, aromatic-substituted aliphatic, aromatic-substituted cycloaliphatic, aromatic-substituted heterocyclic, heterocyclic-substituted aliphatic, heterocyclic-substituted alicyclic, and heterocyclic-substituted aromatic amines and may be saturated or unsaturated. The amines may also contain non-hydrocarbon substituents or groups as long as these groups do not significantly interfere with the reaction of the amines with the acylating reagents of this invention. Such non-hydrocarbon substituents or groups include lower alkoxy, lower alkyl mercapto, nitro, interrupting groups such as —O— and —S—(e.g., as in such groups as —$CH_2$—, $CH_2$—X—$CH_2CH_2$— where X is —O— or —S—).

With the exception of the branched polyalkylene polyamine, the polyoxyalkylene polyamines, and the high molecular weight hydrocarbyl-substituted amines described more fully hereafter, the amines ordinarily contain less than about 40 carbon atoms in total and usually not more than about 20 carbon atoms in total.

Aliphatic monoamines include mono-aliphatic and di-aliphatic substituted amines wherein the aliphatic groups can be saturated or unsaturated and straight or branched chain. Thus, they are primary or secondary aliphatic amines. Such amines include, for example, mono- and di-alkyl-substituted amines, mono- and di-alkenyl-substituted amines, and amines having one N-alkenyl substituent and one N-alkyl substituent and the like. The total number of carbon atoms in these aliphatic monoamines will, as mentioned before, normally not exceed about 40 and usually not exceed about 20 carbon atoms. Specific examples of such monoamines include ethylamine, diethylamine, n-butylamine, di-n-butylamine, allylamine, isobutylamine, cocoamine, stearylamine, laurylamine, methyllaurylamine, oleylamine, N-methyl-octylamine, dodecylamine, octadecylamine, and the like.

Aromatic amines include those monoamines wherein a carbon atom of the aromatic ring structure is attached directly to the amino nitrogen. The aromatic ring will usually be a mononuclear aromatic ring (i.e., one derived from benzene) but can include fused aromatic rings, especially those derived from naphthalene. Examples of aromatic monoamines include aniline, di(paramethylphenyl) amine, naphthylamine, N-(n-butyl)aniline, and the like.

Examples of aliphatic-substituted, cycloaliphatic-substituted, and heterocyclic-substituted aromatic monoamines are para-ethoxyaniline, para-dodecylaniline, cyclohexyl-substituted naphthylamine, and thienyl-substituted aniline.

Polyamines are aliphatic, cycloaliphatic and aromatic polyamines analogous to the above-described monoamines except for the presence within their structure of additional amino nitrogens. The additional amino nitrogens can be primary, secondary or tertiary amino nitrogens. Examples of such polyamines include N-amino-propyl-cyclohexylamines, N,N'-di-n-butyl-para-phenylene diamine, bis-(para-aminophenyl)methane, 1,4-diaminocyclohexane, and the like.

Heterocyclic mono- and polyamines can also be used in making the carboxylic derivative compositions (B). As used herein, the terminology "heterocyclic mono- and polyamine (s)" is intended to describe those heterocyclic amines containing at least one primary or secondary amino group and at least one nitrogen as a heteroatom in the heterocyclic ring. However, as long as there is present in the heterocyclic mono- and polyamines at least one primary or secondary amino group, the hetero-N atom in the ring can be a tertiary amino nitrogen; that is, one that does not have hydrogen attached directly to the ring nitrogen. Heterocyclic amines can be saturated or unsaturated and can contain various substituents such as nitro, alkoxy, alkyl mercapto, alkyl, alkenyl, aryl, alkaryl, or aralkyl substituents. Generally, the total number of carbon atoms in the substituents will not exceed about 20. Heterocyclic amines can contain hetero atoms other than nitrogen, especially oxygen and sulfur. Obviously they can contain more than one nitrogen hetero atom. The five- and six-membered heterocyclic rings are preferred.

Hydroxy-substituted mono- and polyamines, analogous to the mono- and polyamines described above are also useful in preparing carboxylic derivative (B) provided they contain at least one primary or secondary amino group. Hydroxy-substituted amines having only tertiary amino nitrogen such as in tri-hydroxyethyl amine, are thus excluded as amine reactants but can be used as alcohols in preparing component (E) as disclosed hereinafter. The hydroxy-substituted amines contemplated are those having hydroxy substituents bonded directly to a carbon atom other than a carbonyl carbon atom; that is, they have hydroxy groups capable of functioning as alcohols. Examples of such hydroxy-substituted amines include ethanolamine, di-(3-hydroxypropyl)-amine, 3-hydroxybutyl-amine, 4-hydroxybutyl-amine, diethanolamine, di-(2-hydroxypropyl)-amine, N-(hydroxypropyl)-propylamine, N-(2-hydroxyethyl)-cyclohexylamine, 3-hydroxy-cyclopentylamine, parahydroxyaniline, N-hydroxyethyl piperazine, and the like.

Hydrazine and substituted-hydrazine can also be used. At least one of the nitrogens in the hydrazine must contain a hydrogen directly bonded thereto. Preferably there are at least two hydrogens bonded directly to hydrazine nitrogen and, more preferably, both hydrogens are on the same nitrogen. The substituents which may be present on the hydrazine include alkyl, alkenyl, aryl, aralkyl, alkaryl, and the like. Usually, the substituents are alkyl, especially lower alkyl, phenyl, and substituted phenyl such as lower alkoxy substituted phenyl or lower alkyl substituted phenyl. Specific examples of substituted hydrazines are methylhydrazine, N,N-dimethyl-hydrazine, N,N'-dimethylhydrazine, phenylhydrazine and N-phenyl-N'-ethylhydrazine.

The high molecular weight hydrocarbyl amines, both mono-amines and polyamines, which can be used are generally prepared by reacting a chlorinated polyolefin having a molecular weight of at least about 400 with ammonia or amine. Such amines are known in the art and described, for example, in U.S. Pat. Nos. 3,275,554 and 3,438,757, both of which are expressly incorporated herein by reference for their disclosure in regard to how to prepare these amines. All that is required for use of these amines is that they possess at least one primary or secondary amino group.

Suitable amines also include polyoxyalkylene polyamines, e.g., polyoxyalkylene diamines and polyoxyalkylene triamines, having average molecular weights ranging from about 200 to 4000 and preferably from about 400 to 2000.

The preferred polyoxyalkylene polyamines include the polyoxyethylene and polyoxypropylene diamines and the polyoxypropylene triamines having average molecular weights ranging from about 200 to 2000. The polyoxyalkylene polyamines are commercially available and may be obtained, for example, from the Jefferson Chemical Company, Inc. under the trade name "Jeffamines D-230, D-400, D-1000, D-2000, T-403, etc.".

U.S. Pat. Nos. 3,804,763 and 3,948,800 are expressly incorporated herein by reference for their disclosure of such polyoxyalkylene polyamines and process for acylating them with carboxylic acid acylating agents which processes can be applied to their reaction with the acylating reagents and carboxylic esters used in this invention.

The most preferred amines are the alkylene polyamines, including the polyalkylene polyamines. The alkylene polyamines include those conforming to the formula

  (VII)

wherein n is from 1 to about 10; each $R_3$ is independently a hydrogen atom, a hydrocarbyl group or a hydroxy-substituted or an amino-substituted hydrocarbyl group having up to about 30 atoms, with the proviso that at least one $R_3$ group is a hydrogen atom and U is an alkylene group of about 2 to about 10 carbon atoms. Preferably U is ethylene or propylene. Especially preferred are the alkylene polyamines where each $R_3$ is independently hydrogen or an amino-substituted hydrocarbyl group, with the ethylene polyamines and mixtures of ethylene polyamines being the most preferred. Usually n will have an average value of from about 2 to about 7. Such alkylene polyamines include methylene polyamine, ethylene polyamines, butylene polyamines, propylene polyamines, pentylene polyamines, hexylene polyamines, heptylene polyamines, etc. The higher homologs of such amines and related amino alkyl-substituted piperazines are also included.

The alkylene polyamines include ethylene diamine, triethylene tetramine, propylene diamine, trimethylene diamine, hexamethylene diamine, decamethylene diamine, hexamethylene diamine, decamethylene diamine, octamethylene diamine, di(heptamethylene) triamine, tripropylene tetramine, tetraethylene pentamine, trimethylene diamine, pentaethylene hexamine, di(trimethylene) triamine, N-(2-aminoethyl)piperazine, 1,4-bis(2, aminoethyl)piperazine, and the like. Higher homologs as are obtained by condensing two or more of the above-illustrated alkylene amines are useful, as are mixtures of two or more of any of the afore-described polyamines.

Ethylene polyamines, such as those mentioned above, are especially useful for reasons of cost and effectiveness. Such polyamines are described in detail under the heading "Diamines and Higher Amines" in The Encyclopedia of Chemical Technology, Second Edition, Kirk and Othmer, Volume 7, pages 27–39, Interscience Publishers, Division of John Wiley and Sons, 1965, which is hereby incorporated by reference for the disclosure of useful polyamines. Such compounds are prepared most conveniently by the reaction of an alkylene chloride with ammonia or by reaction of an ethylene imine with a ring-opening reagent such as ammonia, etc. These reactions result in the production of the somewhat complex mixtures of alkylene polyamines, including cyclic condensation products such as piperazines. The mixtures are particularly useful in preparing the carboxylic derivatives (B) of this invention. On the other hand, quite satisfactory products can also be obtained by the use of pure alkylene polyamines.

Other useful types of polyamine mixtures are those resulting from stripping of the above-described polyamine mixtures. In this instance, lower molecular weight polyamines and volatile contaminants are removed from an alkylene polyamine mixture to leave as residue what is often termed "polyamine bottoms". In general, alkylene polyamine bottoms can be characterized as having less than two, usually less than 1% (by weight) material boiling below about 200° C. In the instance of ethylene polyamine bottoms, which are readily available and found to be quite useful, the bottoms contain less than about 2% (by weight) total diethylene triamine (DETA) or triethylene tetramine (TETA). A typical sample of such ethylene polyamine bottoms obtained from the Dow Chemical Company of Freeport, Tex. designated "E-100" showed a specific gravity at 15.6° C. of 1.0168, a percent nitrogen by weight of 33.15 and a viscosity at 40° C. of 121 centistokes. Gas chromatography analysis of such a sample showed it to contain about 0.93% "Light Ends" (most probably DETA), 0.72% TETA, 21.74% tetraethylene pentamine and 76.61% pentaethylene hexamine and higher (by weight). These alkylene polyamine bottoms include cyclic condensation products such as piperazine and higher analogs of diethylene triamine, triethylene tetramine and the like.

The carboxylic esters which are useful as component (A-2-b) are known in the art, and the preparation of a number of these derivatives is described in, for example, U.S. Pat. Nos. 3,957,854 and 4,234,435 which are hereby incorporated by reference. The following specific examples illustrate the preparation of the esters wherein both alcohols and amines are reacted with the acylating agent.

EXAMPLE E-13

A mixture of 334 parts (0.52 equivalent) of the polyisobutene-substituted succinic acylating agent prepared in Example E-2, 548 parts of mineral oil, 30 parts (0.88 equivalent) of pentaerythritol and 8.6 parts (0.0057 equivalent) of Polyglycol 112-2 demulsifier from Dow Chemical Company is heated at 150° C. for 2.5 hours. The reaction mixture is heated to 210° C. in 5 hours and held at 210° C. for 3.2 hours. The reaction mixture is cooled to 190° C. and 8.5 parts (0.2 equivalent) of a commercial mixture of ethylene polyamines having an average of about 3 to about 10 nitrogen atoms per molecule are added. The reaction mixture is stripped by heating at 205° C. with nitrogen blowing for 3 hours, then filtered to yield the filtrate as an oil solution of the desired product.

EXAMPLE E-14

A mixture is prepared by the addition of 14 parts of aminopropyl diethanolamine to 867 parts of the oil solution of the product prepared in Example E-1 at 190°–200° C. The reaction mixture is held at 195° C. for 2.25 hours, then cooled to 120° C. and filtered. The filtrate is an oil solution of the desired product.

EXAMPLE E-15

A mixture is prepared by the addition of 7.5 parts of piperazine to 867 parts of the oil solution of the product prepared in Example E-11 at 190° C. The reaction mixture is heated at 190°–205° C. for 2 hours, then cooled to 130° C. and filtered. The filtrate is an oil solution of the desired product.

EXAMPLE E-16

A mixture of 322 parts (0.5 equivalent) of the polyisobutene-substituted succinic acylating agent prepared in Example E-2, 68 parts (2.0 equivalents) of pentaerythritol and 508 parts of mineral oil is heated at 204°–227° C. for 5 hours. The reaction mixture is cooled to 162° C. and 5.3 parts (0.13 equivalent) of a commercial ethylene polyamine mixture having an average of about 3 to 10 nitrogen atoms per molecule is added. The reaction mixture is heated at 162°–163° C. for one hour, then cooled to 130° C. and filtered. The filtrate is an oil solution of the desired product.

EXAMPLE E-17

The procedure for Example E-16 is repeated except the 5.3 parts (0.13 equivalent) of ethylene polyamine is replaced by 21 parts (0.175 equivalent) of tris-(hydroxymethyl) aminomethane.

EXAMPLE E-18

A mixture of 1480 parts of the polyisobutene-substituted succinic acylating agent prepared in Example E-6, 115 parts (0.53 equivalent) of a commercial mixture of $C_{12-18}$ straight-chain primary alcohols, 87 parts (0.594 equivalent) of a commercial mixture of $C_{8-10}$ straight-chain primary alcohols, 1098 parts of mineral oil and 400 parts of toluene is heated to 120° C. At 120° C., 1.5 parts of sulfuric acid are added and the reaction mixture is heated to 160° C. and held for 3 hours. To the reaction mixture are then added 158 parts (2.0 equivalents) of n-butanol and 1.5 parts of sulfuric acid. The reaction mixture is heated at 160° C. for 15 hours, and 12.6 parts (0.088 equivalent) of aminopropyl morpholine are added. The reaction mixture is held at 160° C. for an additional 6 hours, stripped at 150° C. under vacuum and filtered to yield an oil solution of the desired product.

EXAMPLE E-19

(A) A mixture of 1000 parts of polyisobutene having a number average molecular weight of about 1000 and 108 parts (1.1 moles) of maleic anhydride is heated to about 190° C. and 100 parts (1.43 moles) of chlorine are added beneath the surface over a period of about 4 hours while maintaining the temperature at about 185°–190° C. The mixture then is blown with nitrogen at this temperature for several hours, and the residue is the desired polyisobutene-substituted succinic acylating agent. (B) A solution of 1000 parts of the above-prepared acylating agent in 857 parts of mineral oil is heated to about 150° C. with stirring, and 109 parts (3.2 equivalents) of pentaerythritol are added with stirring. The mixture is blown with nitrogen and heated to about 200° C. over a period of about 14 hours to form an oil solution of the desired carboxylic ester intermediate. To the intermediate, there are added 19.25 parts (46 equivalent) of a commercial mixture of ethylene polyamines having an average of about 3 to about 10 nitrogen atoms per molecule. The reaction mixture is stripped by heating at 205° C. with nitrogen blowing for 3 hours and filtered. The filtrate is an oil solution (45% oil) of the desired amine-modified carboxylic ester which contains 0.35% nitrogen.

EXAMPLE E-20

(A) A mixture of 1000 parts (0.495 mole) of polyisobutene having a number average molecular weight of 2020 and a weight average molecular weight of 6049 and 115 parts (1.17 moles) of maleic anhydride is heated to 184° C. over 6 hours, during which time 85 parts (1.2 moles) of chlorine are added beneath the surface. An additional 59 parts (0.83 mole) of chlorine are added over 4 hours at 184°–189° C. The mixture is blown with nitrogen at 186°–190° C. for 26 hours. The residue is a polyisobutene-substituted succinic anhydride having a total acid number of 95.3.

(B) A solution of 409 parts (0.66 equivalent) of the substituted succinic anhydride in 191 parts of mineral oil is heated to 150° C. and 42.5 parts (1.19 equivalent) of pentaerythritol are added over 10 minutes, with stirring, at 145°–150° C. The mixture is blown with nitrogen and heated to 205°–210° C. over about 14 hours to yield an oil solution of the desired polyester intermediate.

Diethylene triamine, 4.74 parts (0.138 equivalent), is added over one-half hour at 160° C. with stirring, to 988 parts of the polyester intermediate (containing 0.69 equivalent of substituted succinic acylating agent and 1.24 equivalents of pentaerythritol). Stirring is continued at 160° C. for one hour, after which 289 parts of mineral oil are added. The mixture is heated for 16 hours at 135° C. and filtered at the same temperature, using a filter aid material. The filtrate is a 35% solution in mineral oil of the desired amine-modified polyester. It has a nitrogen content of 0.16% and a residual acid number of 2.0.

EXAMPLE E-21

Following the procedure of Example E-20, 988 parts of the polyester intermediate of that example are reacted with 5 parts (0.138 equivalent) of triethylene tetramine. The product is diluted with 290 parts of mineral oil to yield a 35% solution of the desired amine-modified polyester. It contains 0.15% nitrogen and has a residual acid number of 2.7.

EXAMPLE E-22

Pentaerythritol, 42.5 parts (1.19 equivalents) is added over 5 minutes at 150° C. to a solution in 208 parts of mineral oil of 448 parts (0.7 equivalent) of a polyisobutene-substituted succinic anhydride similar to that of Example E-20 but having a total acid number of 92. The mixture is heated to 205° C. over 10 hours and blown with nitrogen for 6 hours at 205°–210° C. It is then diluted with 384 parts of mineral oil and cooled to 165° C., and 5.89 parts (0.14 equivalent) of a commercial ethylene polyamine mixture containing an average of 3-7 nitrogen atoms per molecule are added over 30 minutes at 155°–160° C. Nitrogen blowing is continued for one hour, after which the mixture is diluted with an additional 304 parts of oil. Mixing is continued at 130°–135° C. for 15 hours after which the mixture is cooled and filtered using a filter aid material. The filtrate is a 35% solution in mineral oil of the desired amine-modified polyester. It contains 0.147% nitrogen and has a residual acid number of 2.07.

EXAMPLE E-23

A solution of 417 parts (0.7 equivalent) of the polyisobutene-substituted succinic anhydride of Example E-20 in 194 parts of mineral oil is heated to 153° C. and 42.8 parts (1.26 equivalents) of pentaerythritol are added. The mixture is heated at 153°–228° C. for about 6 hours. It is then cooled to 170° C. and diluted with 375 parts of mineral oil. It is further cooled to 156°–158° C. and 5.9 parts (0.14 equivalent) of the ethylene polamine mixture of Example E-22 are added over one-half hour. The mixture is stirred at 158°–160° C. for one hour and diluted with an additional 295 parts of mineral oil. It is blown with nitrogen at 135° C. for 16 hours and filtered at 135° C. using a filter aid material. The filtrate is the desired 35% solution in mineral oil of the amine-modified polyester. It contains 0.16% nitrogen and has a total acid number of 2.0.

The above-described acylated amines and carboxylic esters are effective ashless dispersants in the present invention. In another embodiment, these compositions may be considered as intermediates and post-treated with one or more post-treating reagents selected from the group consisting of boron trioxide, boron anhydrides, boron halides, boron acids, boron amides, esters of boric acids, carbon disulfide, hydrogen sulfide, sulfur, sulfur chlorides, alkenyl cyanides, carboxylic acid acylating agents, aldehydes, ketones, urea, thiourea, guanidine, dicyanodiamide, hydrocarbyl phosphates, hydrocarbyl phosphites, hydrocarbyl thiophosphates, hydrocarbyl thiophosphites, phosphorus sulfides, phosphorus oxides, phosphoric acid, hydrocarbyl thiocyanates, hydrocarbyl isocyanates, hydrocarbyl isothiocyanates, epoxides, episulfides, formaldehyde or formaldehyde-producing compounds with phenols, and sulfur with phenols. These post-treating reagents can be used with carboxylic derivative compositions prepared from the acylating reagents and a combination of amines and alcohols as described above.

Since processes involving the use of these post-treating reagents are known insofar as application to reaction products of high molecular weight carboxylic acid acylating agents and amines and/or alcohols, a detailed description of these processes herein is believed unnecessary. The following U.S. Patents are expressly incorporated herein by reference for their disclosure of post-treating processes and post-treating reagents applicable to the carboxylic derivative compositions useful in this invention: U.S. Pat. No. Nos. 3,087,936; 3,254,025; 3,256,185; 3,278,550; 3,282,955; 3,284,410; 3,338,832; 3,533,945; 3,639,242; 3,708,522; 3,859,318; 3,865,813; etc. U.K. Patent Nos. 1,085,903 and 1,162,436 also describe such processes.

(A-2-c) The Neutral and Basic Alkali Metal and Alkaline Earth Metal Salts.

The oil solutions used in the present invention also may contain, and preferably do contain, at least one neutral or basic alkali metal or alkaline earth metal salt of at least one acidic organic compound. Such salt compounds generally are referred to as ash-containing detergents. The acidic organic compound may be at least one sulfur acid, carboxylic acid, phosphorus acid, or phenol, or mixtures thereof.

The alkali metals include lithium, sodium and potassium, with sodium and potassium being preferred. Calcium, magnesium, barium and strontium are the preferred alkaline earth metals. Salts containing a mixture of ions of two or more of these alkaline earth metals can be used.

The salts which are useful as component (A-2-c) can be neutral or basic. The neutral salts contain an amount of metal which is just sufficient to neutralize the acidic groups present in the salt anion, and the basic salts contain an excess of the metal cation. Generally, the basic or overbased salts are preferred. The basic or overbased salts will have metal ratios of up to about 40 and more particularly from about 2 to about 30 or 40.

A commonly employed method for preparing the basic (or overbased) salts comprises heating a mineral oil solution of the acid with a stoichiometric excess of a metal neutralizing agent, e.g., a metal oxide, hydroxide, carbonate, bicarbonate, sulfide, etc., at temperatures above about 500° C. In addition, various promoters may be used in the neutralizing process to aid in the incorporation of the large excess of metal. These promoters include such compounds as the phenolic substances, e.g., phenol, naphthol, alkylphenol, thiophenol, sulfurized alkylphenol and the various condensation products of formaldehyde with a phenolic substance; alcohols such as methanol, 2-propanol, octyl alcohol, cellosolve carbitol, ethylene, glycol, stearyl alcohol, and cyclohexyl alcohol; amines such as aniline, phenylenediamine, phenothiazine, phenyl-beta-naphthylamine, and dodecyl amine, etc. A particularly effective process for preparing the basic alkaline earth metal salts comprises mixing the acid with an excess of the basic alkaline earth metal in the presence of the phenolic promoter and a small amount of water and carbonating the mixture at an elevated temperature, e.g., 60° C. to about 200° C.

A general description of some of the basic alkali metal salts is contained in U.S. Pat. No. 4,326,972 (Chamberlin). This patent is hereby incorporated by reference for its disclosure of useful alkali metal salts and methods of preparing said salts.

As mentioned above, the acidic organic compound from which the salt (A-2-c) is derived may be at least one sulfur acid, carboxylic acid, phosphorus acid, or phenol or mixtures thereof. The sulfur acids include the sulfonic acids, thiosulfonic, sulfinic, sulfenic, partial ester sulfuric, sulfurous and thiosulfuric acids.

The sulfonic acids which are useful in preparing component (A-2-c) include those represented by the formulae

   (VIII)

and

   (IX)

In these formulae, R'" is an aliphatic or aliphatic-substituted cycloaliphatic hydrocarbon or essentially hydrocarbon group free from acetylenic unsaturation and containing up to about 60 carbon atoms. When R'" is aliphatic, it usually contains at least about 15 carbon atoms; when it is an aliphatic-substituted cycloaliphatic group, the aliphatic substituents usually contain a total of at least about 12 carbon atoms. Examples of R'" are alkyl, alkenyl and alkoxyalkyl radicals, and aliphatic-substituted cycloaliphatic groups wherein the aliphatic substituents are alkyl, alkenyl, alkoxy, alkoxyalkyl, carboxyalkyl and the like. Generally, the cycloaliphatic nucleus is derived from a cycloalkane or a cycloalkene such as cyclopentane, cyclohexane, cyclohexene or cyclopentene. Specific examples of R'" are cetylcyclohexyl, laurylcyclohexyl, cetyloxyethyl, octadecenyl, and groups derived from petroleum, saturated and unsaturated paraffin wax, and olefin polymers including polymerized monoolefins and diolefins containing about 2–8 carbon atoms per olefinic monomer unit. R' can also contain other substituents such as phenyl, cycloalkyl, hydroxy, mercapto, halo, nitro, amino, nitroso, lower alkoxy, lower alkylmercapto, carboxy, carbalkoxy, oxo or thio, or interrupting groups such as —NH—, —O— or —S—, as long as the essentially hydrocarbon character thereof is not destroyed.

R" in Formula VIII is generally a hydrocarbon or essentially hydrocarbon group free from acetylenic unsaturation and containing from about 4 to about 60 aliphatic carbon atoms, preferably an aliphatic hydrocarbon group such as alkyl or alkenyl. It may also, however, contain substituents or interrupting groups such as those enumerated above provided the essentially hydrocarbon character thereof is retained. In general, any non-carbon atoms present in R''' or R" do not account for more than 10% of the total weight thereof.

T is a cyclic nucleus which may be derived from an aromatic hydrocarbon such as benzene, naphthalene, anthracene or biphenyl, or from a heterocyclic compound such as pyridine, indole or isoindole. Ordinarily, T is an aromatic hydrocarbon nucleus, especially a benzene or naphthalene nucleus.

The subscript x is at least 1 and is generally 1–3. The subscripts r and y have an average value of about 1–2 per molecule and are generally also 1.

The sulfonic acids are generally petroleum sulfonic acids or synthetically prepared alkaryl sulfonic acids. Among the petroleum sulfonic acids, the most useful products are those prepared by the sulfonation of suitable petroleum fractions with a subsequent removal of acid sludge, and purification. Synthetic alkaryl sulfonic acids are prepared usually from alkylated benzenes such as the Friedel—Crafts reaction products of benzene and polymers such as tetrapropylene. The following are specific examples of sulfonic acids useful in preparing the salts (A-2-c). It is to be understood that such examples serve also to illustrate the salts of such sulfonic acids useful as component (A-2-c). In other words, for every sulfonic acid enumerated, it is intended that the corresponding neutral and basic alkali metal and alkaline earth metal salts thereof are also understood to be illustrated. (The same applies to the lists of carboxylic acid phosphonic acid and phenol materials listed below.) Such sulfonic acids include mahogany sulfonic acids, bright stock sulfonic acids, petrolatum sulfonic acids, mono- and polywax-substituted naphthalene sulfonic acids, cetylchlorobenzene sulfonic acids, cetylphenol sulfonic acids, cetylphenol disulfide sulfonic acids, cetoxycapryl benzene sulfonic acids, dicetyl thianthrene sulfonic acids, dilauryl beta-naphthol sulfonic acids, dicapryl nitronaphthalene sulfonic acids, saturated paraffin wax sulfonic acids, unsaturated paraffin wax sulfonic acids, hydroxy-substituted paraffin wax sulfonic acids, tetraisobutylene sulfonic acids, tetra-amylene sulfonic acids, chloro-substituted paraffin wax sulfonic acids, nitroso-substituted paraffin wax sulfonic acids, petroleum naphthene sulfonic acids, cetylcyclopentyl sulfonic acids, lauryl cyclohexyl sulfonic acids, mono- and polywax-substituted cyclohexyl sulfonic acids, dodecylbenzene sulfonic acids, "dimer alkylate" sulfonic acids, and the like.

Alkyl-substituted benzene sulfonic acids wherein the alkyl group contains at least 8 carbon atoms including dodecyl benzene "bottoms" sulfonic acids are particularly useful. The latter are acids derived from benzene which has been alkylated with propylene tetramers or isobutene trimers to introduce 1, 2, 3, or more branched-chain $C_{12}$ substituents on the benzene ring. Dodecyl benzene bottoms, principally mixtures of mono-and di-dodecyl benzenes, are available as by-products from the manufacture of household detergents. Similar products obtained from alkylation bottoms formed during manufacture of linear alkyl sulfonates (LAS) are also useful in making the sulfonates used in this invention.

The production of sulfonates from detergent manufacture by-products by reaction with, e.g., $SO_3$, is well known to those skilled in the art. See, for example, the article "Sulfonates" in Kirk-Othmer, *Encyclopedia of Chemical Technology*, Second Edition, Vol. 19, pp. 291 et seq. published by John Wiley & Sons, N.Y. (1969).

Other descriptions of basic sulfonate salts which can be incorporated into the oil solutions of this invention as component (A-2-c), and techniques for making them can be found in the following U.S. Pat. Nos. 2,174,110; 2,202,781; 2,239,974; 2,319,121; 2,337,552; 3,488,284; 3,595,790; and 3,798,012. These are hereby incorporated by reference for their disclosures in this regard.

Suitable carboxylic acids from which useful metal salts can be prepared include aliphatic, cycloaliphatic and aromatic mono- and polybasic carboxylic acids free from acetylenic unsaturation, including naphthenic acids, alkyl- or alkenyl-substituted cyclopentanoic acids, alkyl- or alkenyl-substituted cyclohexanoic acids, and alkyl- or alkenyl-substituted aromatic carboxylic acids. The aliphatic acids generally contain from about 8 to about 50, and preferably from about 12 to about 25 carbon atoms. The cycloaliphatic and aliphatic carboxylic acids are preferred, and they can be saturated or unsaturated. Specific examples include 2-ethylhexanoic acid, linolenic acid, propylene tetramer-substituted maleic acid, behenic acid, isostearic acid, pelargonic acid, capric acid, palmitoleic acid, linoleic acid, lauric acid, oleic acid, ricinoleic acid, undecyclic acid, dioctylcyclopentanecarboxylic acid, myristic acid, dilauryldecahydronaphthalene-carboxylic acid, stearyl-octahydroindenecarboxylic acid, palmitic acid, alkyl- and alkenylsuccinic acids, acids formed by oxidation of petrolatum or of hydrocarbon waxes, and commercially available mixtures of two or more carboxylic acids such as tall oil acids, rosin acids, and the like.

The equivalent weight of the acidic organic compound is its molecular weight divided by the number of acidic groups (i.e., sulfonic acid or carboxy groups) present per molecule.

The pentavalent phosphorus acids useful in the preparation of the salts (A-2-c) may be represented by the formula

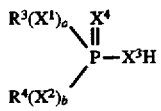

wherein each of $R^3$ and $R^4$ is hydrogen or a hydrocarbon or essentially hydrocarbon group preferably having from about 4 to about 25 carbon atoms, at least one of $R^3$ and $R^4$ being hydrocarbon or essentially hydrocarbon; each of $X^1$, $X^2$, $X^3$ and $X^4$ is oxygen or sulfur; and each of a and b is 0 or 1. Thus, it will be appreciated that the phosphorus acid may be an organophosphoric, phosphonic or phosphinic acid, or a thio analog of any of these.

The phosphorus acids may be those of the formula

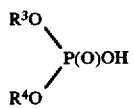

wherein $R^3$ is a phenyl group or (preferably) an alkyl group having up to 18 carbon atoms, and $R^4$ is hydrogen or a similar phenyl or alkyl group. Mixtures of such phosphorus acids are often preferred because of their ease of preparation.

Salt (A-2-c) may also be prepared from phenols; that is, compounds containing a hydroxy group bound directly to an aromatic ring. The term "phenol" as used herein includes compounds having more than one hydroxy group bound to an aromatic ring, such as catechol, resorcinol and hydroquinone. It also includes alkylphenols such as the cresols and ethylphenols, and alkenylphenols. Preferred are phenols containing at least one alkyl substituent containing about 3-100 and especially about 6-50 carbon atoms, such as heptylphenol, octylphenol, dodecylphenol, tetrapropene-alkylated phenol, octadecylphenol and polybutenylphenols. Phenols containing more than one alkyl substituent may also be used, but the monoalkylphenols are preferred because of their availability and ease of production.

Also useful are condensation products of the above-described phenols with at least one lower aldehyde or ketone, the term "lower" denoting aldehydes and ketones containing not more than 7 carbon atoms. Suitable aldehydes include formaldehyde, acetaldehyde, propionaldehyde, the butyraldehydes, the valeraldehydes and benzaldehyde. Also suitable are aldehyde-yielding reagents such as paraformaldehyde, trioxane, methylol, Methyl Formcel and paraldehyde. Formaldehyde and the formaldehyde-yielding reagents are especially preferred.

In one preferred embodiment, the metal salts (A-2-c) are basic metal salts having metal ratios-of at least about 2 and more generally from about 4 to about 40, preferably from about 6 to about 30 and especially from about 8 to about 25.

In another embodiment, the alkali metal salts (A-2-c)- are basic salts which are oil-soluble dispersions prepared by contacting for a period of time sufficient to form a stable dispersion, at a temperature between the solidification temperature of the reaction mixture and its decomposition temperature:

(C-1) at least one acidic gaseous material selected from the group consisting of carbon dioxide, hydrogen sulfide and sulfur dioxide, with (C-2) a reaction mixture comprising (C-2-a) at least one oil-soluble sulfonic acid, or derivative thereof susceptible to overbasing;

(C-2-b) at least one alkali metal or basic alkali metal compound;

(C-2-c) at least one lower aliphatic alcohol, alkyl phenol, or sulfurized alkyl phenol; and (C-2-d) at least one oil-soluble carboxylic acid or functional derivative thereof.

When (C-2-c) is an alkyl phenol or a sulfurized alkyl phenol, component (C-2-d) is optional. A satisfactory basic sulfonic acid salt can be prepared with or without the carboxylic acid in the mixture (C-2).

Reagent (C-1) is at least one acidic gaseous material which may be carbon dioxide, hydrogen sulfide or sulfur dioxide; mixtures of these gases are also useful. Carbon dioxide is preferred.

As mentioned above, component (C-2) generally is a mixture containing at least four components of which component (C-2-a) is at least one oil-soluble sulfonic acid as previously defined, or a derivative thereof susceptible to overbasing. Mixtures of sulfonic acids and/or their derivatives may also be used. Sulfonic acid derivatives susceptible to overbasing include their metal salts, especially the alkaline earth, zinc and lead salts; ammonium salts and amine salts (e.g., the ethylamine, butylamine and ethylene polyamine salts); and esters such as the ethyl, butyl and glycerol esters.

Component (C-2-b) is at least one alkali metal or a basic compound thereof. Illustrative of basic alkali metal compounds are the hydroxides, alkoxides (typically those in which the alkoxy group contains up to 10 and preferably up to 7 carbon atoms), hydrides and amides. Thus, useful basic alkali metal compounds include sodium hydroxide, potassium hydroxide, lithium hydroxide, sodium propoxide, lithium methoxide, potassium ethoxide, sodium butoxide, lithium hydride, sodium hydride, potassium hydride, lithium amide, sodium amide and potassium amide. Especially preferred are sodium hydroxide and the sodium lower alkoxides (i.e., those containing up to 7 carbon atoms). The equivalent weight of component (C-2-b) for the purpose of this invention is equal to its molecular weight, since the alkali metals are monovalent.

Component (C-2-c) may be at least one lower aliphatic alcohol, preferably a monohydric or dihydric alcohol. Illustrative alcohols are methanol, ethanol, 1-propanol, 1-hexanol, isopropanol, isobutanol, 2-pentanol, 2, 2-dimethyl-1-propanol, ethylene glycol, 1-3-propanediol and 1, 5-pentanediol. The alcohol also may be a glycol ether such as Methyl Cellosolve. Of these, the preferred alcohols are methanol, ethanol and propanol, with methanol being especially preferred.

Component (C-2-c) also may be at least one alkyl phenol or sulfurized alkyl phenol. The sulfurized alkyl phenols are preferred, especially when (C-2-b) is potassium or one of its basic compounds such as potassium hydroxide. As used herein, the term "phenol" includes compounds having more than one hydroxy group bound to an aromatic ring, and the aromatic ring may be a benzyl or naphthyl ring. The term "alkyl phenol" includes mono- and di-alkylated phenols in which each alkyl substituent contains from about 6 to about 100 carbon atoms, preferably about 6 to about 50 carbon atoms.

Illustrative alkyl phenols include heptylphenols, octylphenols, decylphenols, dodecylphenols, polypropylene (Mn of about 150)-substituted phenols, polyisobutene (Mn of about 1200)-substituted phenols, cyclohexyl phenols.

Also useful are condensation products of the above-described phenols with at least one lower aldehyde or ketone, the term "lower" denoting aldehydes and ketones containing not more than 7 carbon atoms. Suitable aldehydes include formaldehyde, acetaldehyde, propionaldehyde, the butyraldehydes, the valeraldehydes and benzaldehyde. Also suitable are aldehyde-yielding reagents such as paraformaldehyde, trioxane, methylol, Methyl Formcel and paraldehyde. Formaldehyde and the formaldehyde-yielding reagents are especially preferred.

The sulfurized alkylphenols include phenol sulfides, disulfides or polysulfides. The sulfurized phenols can be derived from any suitable alkylphenol by technique known to those skilled in the art, and many sulfurized phenols are commercially available. The sulfurized alkylphenols may be prepared by reacting an alkylphenol with elemental sulfur and/or a sulfur monohalide (e.g., sulfur monochloride). This reaction may be conducted in the presence of excess base to result in the salts of the mixture of sulfides, disulfides or polysulfides that may be produced depending upon the reaction conditions. It is the resulting product of this reaction which is used in the preparation of component (C-2). U.S. Pat. Nos. 2,971,940 and 4,309,293 disclose various sulfurized phenols which are illustrative of component (C-2-c), and such disclosures of these patents are hereby incorporated by reference.

The following non-limiting examples illustrate the preparation of alkylphenols and sulfurized alkylphenols useful as component (C-2-c).

EXAMPLE 1-C

While maintaining a temperature of 55° C., 100 parts phenol and 68 parts sulfonated polystyrene catalyst (marketed as Amberlyst-15 by Rohm and Haas Company) are charged to a reactor equipped with a stirrer, condenser, thermometer and subsurface gas inlet tube. The reactor contents are then heated to 120° C. while nitrogen blowing for 2 hours. Propylene tetramer (1232 parts) is charged, and the reaction mixture is stirred at 120° C. for 4 hours. Agitation is stopped, and the batch is allowed to settle for 0.5 hour. The crude supernatant reaction mixture is filtered and vacuum stripped until a maximum of 0.5% residual propylene tetramer remains.

EXAMPLE 2-C

Benzene (217 parts) is added to phenol (324 parts, 3.45 moles) at 38° C. and the mixture is heated to 47° C. Boron trifluoride (8.8 parts, 0.13 mole) is blown into the mixture over a one-half hour period at 38°–52° C. Polyisobutene (1000 parts, 1.0 mole) derived from the polymerization of $C_4$ monomers predominating in isobutylene is added to the mixture at 52°–58° C. over a 3.5 hour period. The mixture is held at 52° C. for 1 additional hour. A 26% solution of aqueous ammonia (15 parts) is added and the mixture is heated to 70° C. over a 2-hour period. The mixture is then filtered and the filtrate is the desired crude polyisobutene-substituted phenol. This intermediate is stripped by heating 1465 parts to 167° C. and the pressure is reduced to 10 mm. as the material is heated to 218° C. in a 6-hour period. A 64% yield of stripped polyisobutene-substituted phenol (Mn= 885) is obtained as the residue.

EXAMPLE 3-C

A reactor equipped with a stirrer, condenser, thermometer and subsurface addition tube is charged with 1000 parts of the reaction product of Example 1-C . The temperature is adjusted to 48°–49° C. and 319 parts sulfur dichloride is added while the temperature is kept below 60° C. The batch is then heated to 88°–93° C. while nitrogen blowing until the acid number (using bromphenol blue indicator) is less than 4.0. Diluent oil (400 parts) is then added, and the mixture is mixed thoroughly.

EXAMPLE 4-C

Following the procedure of Example 3-C , 1000 parts of the reaction product of Example 1-C is reacted with 175 parts of sulfur dichloride. The reaction product is diluted with 400 parts diluent oil.

EXAMPLE 5-C

Following the procedure of Example 3-C , 1000 parts of the reaction product of Example 1-C is reacted with 319 parts of sulfur dichloride. Diluent oil (788 parts) is added to the reaction product, and the materials are mixed thoroughly.

EXAMPLE 6-C

Following the procedure of Example 4-C , 1000 parts of the reaction product of Example 2-C are reacted with 44 parts of sulfur dichloride to produce the sulfurized phenol.

EXAMPLE 7-C

Following the procedure of Example 5-C , 1000 parts of the reaction product of Example 2-C are reacted with 80 parts of sulfur dichloride.

The equivalent weight of component (C-2-c) is its molecular weight divided by the number of hydroxy groups per molecule.

Component (C-2-d) is at least one oil-soluble carboxylic acid as previously described, or functional derivative thereof. Especially suitable carboxylic acids are those of the formula $R^5(COOH)_n$, wherein n is an integer from 1 to 6 and is preferably 1 or 2 and $R^5$ is a saturated or substantially saturated aliphatic radical (preferably a hydrocarbon radical) having at least 8 aliphatic carbon atoms. Depending upon the value of n, $R^5$ will be a monovalent to hexavalent radical.

$R^5$ may contain non-hydrocarbon substituents provided they do not alter substantially its hydrocarbon character. Such substituents are preferably present in amounts of not more than about 20% by weight. Exemplary substituents include the non-hydrocarbon substituents enumerated hereinabove with reference to component (C-2-a). $R^5$ may also contain olefinic unsaturation up to a maximum of about 5% and preferably not more than 2% olefinic linkages based upon the total number of carbonto-carbon covalent linkages present. The number of carbon atoms in $R^5$ is usually about 8–700 depending upon the source of $R^5$. As discussed below, a preferred series of carboxylic acids and derivatives is prepared by reacting an olefin polymer or halogenated olefin polymer with an alpha,beta-unsaturated acid or its anhydride such as acrylic, methacrylic, maleic or fumaric acid or maleic anhydride to form the corresponding substituted acid or derivative thereof. The $R^5$ groups in these products have a number average molecular weight from about 150 to about 10,000 and usually from about 700 to about 5000, as determined, for example, by gel permeation chromatography.

The monocarboxylic acids useful as component (C-2-d) have the formula $R^5COOH$. Examples of such acids are caprylic, capric, palmitic, stearic, isostearic, linoleic and behenic acids. A particularly preferred group of monocarboxylic acids is prepared by the reaction of a halogenated olefin polymer, such as a chlorinated polybutene, with acrylic acid or methacrylic acid.

Suitable dicarboxylic acids include the substituted succinic acids having the formula $$R^6CHCOOH \atop CH_2COOH \qquad (X)$$

wherein $R^6$ is the same as $R^5$ as defined above. $R^6$ may be an olefin polymer-derived group formed by polymerization of such monomers as ethylene, propylene, 1-butene, isobutene, 1-pentene, 2-pentene, 1-hexene and 3-hexene. $R^6$ may also be derived from a high molecular weight substantially saturated petroleum fraction. The hydrocarbon-substituted succinic acids and their derivatives constitute the most preferred class of carboxylic acids for use as component (C-2-d).

The above-described classes of carboxylic acids derived from olefin polymers, and their derivatives, are well known in the art, and methods for their preparation as well as representative examples of the types useful in the present invention are described in detail in a number of U.S. Patents.

Functional derivatives of the above-discussed acids useful as component (C-2-d) include the anhydrides, esters, amides, imides, amidines and metal or ammonium salts. The reaction products of olefin polymer-substituted succinic acids and mono- or polyamines, particularly polyalkylene polyamines, having up to about 10 amino nitrogens are especially suitable. These reaction products generally comprise mixtures of one or more of amides, imides and amidines. The reaction products of polyethylene amines containing up to about 10 nitrogen atoms and polybutene-substituted succinic anhydride wherein the polybutene radical comprises principally isobutene units are particularly useful. Included in this group of functional derivatives are the compositions prepared by post-treating the amine-anhydride reaction product with carbon disulfide, boron compounds, nitriles, urea, thiourea, guanidine, alkylene oxides or the like. The half-amide, half-metal salt and hal-fester, half-metal salt derivatives of such substituted succinic acids are also useful.

Also useful are the esters prepared by the reaction of the substituted acids or anhydrides with a monoor polyhydroxy compound, such as an aliphatic alcohol or a phenol. Preferred are the esters of olefin polymer-substituted succinic acids or anhydrides and polyhydric aliphatic alcohols containing 2–10 hydroxy groups and up to about 40 aliphatic carbon atoms. This class of alcohols includes ethylene glycol, glycerol, sorbitol, pentaeirythritol, polyethylene glycol, diethanolamine, triethanolamine, N,N'-di (hydroxyethyl)ethylene diamine and the like. When the alcohol contains reactive amino groups, the reaction product may comprise products resulting from the reaction of the acid group with both the hydroxy and amino functions. Thus, this reaction mixture can include half-esters, half-amides, esters, amides, and imides.

The ratios of equivalents of the constituents of reagent (C-2) may vary widely. In general, the ratio of component (C-2-b) to (C-2-a) is at least about 4:1 and usually not more than about 40:1, preferably between 6:1 and 30:1 and most preferably between 8:1 and 25:1. While this ratio may sometimes exceed 40:1, such an excess normally will serve no useful purpose.

The ratio of equivalents of component (C-2-c) to component (C-2-a) is between about 1:20 and 80:1, and preferably between about 2:1 and 50:1. As mentioned above, when component (C-2-c) is an alkyl phenol or sulfurized alkyl phenol, the inclusion of the carboxylic acid (C-2-d) is optional. When present in the mixture, the ratio of equivalents of component (C-2-d) to component (C-2-a) generally is from about 1:1 to about 1:20 and preferably from about 1:2 to about 1:10.

Up to about a stoichiometric amount of acidic material (C-1) is reacted with (C-2). In one embodiment, the acidic material is metered into the (C-2) mixture and the reaction is rapid. The rate of addition of (C-1) is not critical, but may have to be reduced if the temperature of the mixture rises too rapidly due to the exothermicity of the reaction.

When (C-2-c) is an alcohol, the reaction temperature is not critical. Generally, it will be between the solidification temperature of the reaction mixture and its decomposition temperature (i.e., the lowest decomposition temperature of any component thereof). Usually, the temperature will be from about 25° C. to about 200° C. and preferably from about 50° C. to about 150° C. Reagents (C-1) and (C-2) are conveniently contacted at the reflux temperature of the mixture. This temperature will obviously depend upon the boiling points of the various components; thus, when methanol is used as component (C-2-c), the contact temperature will be at or below the reflux temperature of methanol.

When reagent (C-2-c) is an alkyl phenol or a sulfurized alkyl phenol, the temperature of the reaction must be at or above the water-diluent azeotrope temperature so that the water formed in the reaction can be removed.

The reaction is ordinarily conducted at atmospheric pressure, although superatmospheric pressure often expedites the reaction and promotes optimum utilization of reagent (C-1). The process can also be carried out at reduced pressure but, for obvious practical reasons, this is rarely done.

The reaction is usually conducted in the presence of a substantially inert, normally liquid organic diluent such as a low viscosity lubricating oil, which functions as both the dispersing and reaction medium. This diluent will comprise at least about 10% of the total weight of the reaction mixture. Ordinarily it will not exceed about 80% by weight, and it is preferably about 30–70% thereof.

Upon completion of the reaction, any solids in the mixture are preferably removed by filtration or other conventional means. Optionally, readily removable diluents, the alcoholic promoters, and water formed during the reaction can be removed by conventional techniques such as distillation. It is usually desirable to remove substantially all water from the reaction mixture since the presence of water may lead to difficulties in filtration and to the formation of undesirable emulsions in fuels and lubricants. Any such water present is readily removed by heating at atmospheric or reduced pressure or by azeotropic distillation. In one preferred embodiment, when basic potassium sulfonates are desired as component (A-2-c), the potassium salt is prepared using carbon dioxide and the sulfurized alkylphenols as component (C-2-c). The use of the sulfurized phenols results in basic salts of higher metal ratios and the formation of more uniform and stable salts.

The chemical structure of the alkali metal salts (A-2-c) is not known with certainty. The basic salts or complexes may be solutions or, more likely, stable dispersions. Alternatively, they may be regarded as "polymeric salts" formed by the reaction of the acidic material, the oil-soluble acid being overbased, and the metal compound. In view of the above, these compositions are most conveniently defined by reference to the method by which they are formed.

The above-described procedures for preparing alkali metal salts of sulfonic acids having a metal ratio of at least about 2 and preferably a metal ratio between about 4 to 40 using alcohols as component (C-2-c) is described in more detail in U.S. Pat. No. 4,326,972 which has been incorporated by reference for the disclosures of such processes.

The preparation of oil-soluble dispersions of alkali metal sulfonates useful as component (A-2-c) in the oil compositions of this invention is illustrated in the following examples.

EXAMPLE S-1

To a solution of 790 parts (1 equivalent) of an alkylated benzenesulfonic acid and 71 parts of polybutenyl succinic anhydride (equivalent weight about 560) containing predominantly isobutene units in 176 parts of mineral oil is added 320 parts (8 equivalents) of sodium hydroxide and 640 parts (20 equivalents) of methanol. The temperature of the mixture increases to 89° C. (reflux) over 10 minutes due to exotherming. During this period, the mixture is blown with carbon dioxide at 4 cfh. (cubic feet/hr.). Carbonation is continued for about 30 minutes as the temperature gradually decreases to 74° C. The methanol and other volatile materials are stripped from the carbonated mixture by blowing nitrogen through it at 2 cfh. while the temperature is slowly increased to 150° C. over 90 minutes. After stripping is completed, the remaining mixture is held at 155°–165° C. for about 30 minutes and filtered to yield an oil solution of the desired basic sodium sulfonate having a metal ratio of about 7.75. This solution contains 12.4% oil.

EXAMPLE S-2

Following the procedure of Example S-1, solution of 780 parts (1 equivalent) of an alkylated benzenesulfonic acid and 119 parts of the polybutenyl succinic anhydride in 442 parts of mineral oil is mixed with 800 parts (20 equivalents) of sodium hydroxide and 704 parts (22 equivalents) of methanol. The mixture is blown with carbon dioxide at 7 cfh. for 11 minutes as the temperature slowly increases to 97° C. The rate of carbon dioxide flow is reduced to 6 cfh. and the temperature decreases slowly to 88° C. over about 40 minutes. The rate of carbon dioxide flow is reduced to 5 cfh. for about 35 minutes and the temperature slowly decreases to 73° C. The volatile materials are stripped by blowing nitrogen through the carbonated mixture at 2 cfh. for 105 minutes as the temperature is slowly increased to 160° C. After stripping is completed, the mixture is held at 160° C. for an additional 45 minutes and then filtered to yield an oil solution of the desired basic sodium sulfonate hav- ing a metal ratio of about 19.75. This solution contains 18.7% oil.

EXAMPLE S-3

Following the procedure of Example S-1, solution of 3120 parts (4 equivalents) of an alkylated benzenesulfonic acid and 284 parts of the polybutenyl succinic anhydride in 704 parts of mineral oil is mixed with 1280 parts (32 equivalents) of sodium hydroxide and 2560 parts (80 equivalents) of methanol. The mixture is blown with carbon dioxide at 10 cfh. for 65 minutes as the temperature increases to 90° C. and then slowly decreases to 70° C. The volatile material is stripped by blowing nitrogen at 2 cfh. for 2 hours as the temperature is slowly increased to 160° C. After stripping is completed, the mixture is held at 160° C. for 0.5 hour, and then filtered to yield an oil solution of the desired basic sodium sulfonate having a metal ratio of about 7.75. This solution contains 12.35% oil content.

EXAMPLE S-4

Following the procedure of Example S-1, a solution of 3200 parts (4 equivalents) of an alkylated benzenesulfonic acid and 284 parts of the polybutenyl succinic anhydride in 623 parts of mineral oil is mixed with 1280 parts (32 equivalents) of sodium hydroxide and 2560 parts (80 equivalents) of methanol. The mixture is blown with carbon dioxide at 10 cfh. for about 77 minutes. During this time the temperature increases to 92° C. and then gradually drops to 73° C. The volatile materials are stripped by blowing with nitrogen gas at 2 cfh. for about 2 hours as the temperature of the reaction mixture is slowly increased to 160° C. The final traces of volatile material are vacuum stripped and the residue is held at 170° C. and then filtered to yield a clear oil solution of the desired sodium salt, having a metal ratio of about 7.72. This solution has an oil content of 11%.

EXAMPLE S-5

Following the procedure of Example S-1, a solution of 780 parts (1 equivalent) of an alkylated benzenesulfonic acid and 86 parts of the polybutenyl succinic anhydride in 254 parts of mineral oil is mixed with 480 parts (12 equivalents) of sodium hydroxide and 640 parts (20 equivalents) of methanol. The reaction mixture is blown with carbon dioxide at 6 cfh. for about 45 minutes. During this time the temperature increases to 95° C. and then gradually decreases to 74° C. The volatile material is stripped by blowing with nitrogen gas at 2 cfh. for about one hour as the temperature is increased to 160° C. After stripping is complete the mixture is held at 160° C. for 0.5 hour and then filtered to yield an oil solution of the desired sodium salt, having a metal ratio of 11.8. The oil content of this solution is 14.7%.

EXAMPLE S-6

Following the procedure of Example S-1, a solution of 3120 parts (4 equivalents) of an alkylated benzenesulfonic acid and 344 parts of the polybutenyl succinic anhydride in 1016 parts of mineral oil is mixed with 1920 parts (48 equivalents) of sodium hydroxide and 2560 parts (80 equivalents) of methanol. The mixture is blown with carbon dioxide at 10 cfh. for about 2 hours. During this time the temperature increases to 96° C. and then gradually drops to 74° C. The volatile materials are stripped by blowing with nitrogen gas at 2 cfh. for about 2 hours as the temperature is increased from 74° C. to 160° C. by external heating. The stripped mixture is heated for an additional hour at 160° C. and filtered. The filtrate is vacuum stripped to remove a small amount of water, and again filtered to give a solution of the desired sodium salt, having a metal ratio of about 11.8. The oil content of this solution is 14.7%.

EXAMPLE S-7

Following the procedure of Example S-1, a solution of 2800 parts (3.5 equivalents) of an alkylated benzenesulfonic acid and 302 parts of the polybutenyl succinic anhydride in 818 parts of mineral oil is mixed with 1680 parts (42 equivalents) of sodium hydroxide and 2240 parts (70 equivalents) of methanol. The mixture is blown with carbon dioxide for about 90 minutes at 10 cfh. During this period, the temperature increases to 96° C. and then slowly drops to 760° C. The volatile materials are stripped by blowing with nitrogen at 2 cfh. as the temperature is slowly increased from 76° C. to 165° C. by external heating. Water is removed by vacuum stripping. Upon filtration, an oil solution of the desired basic sodium salt is obtained. It has a metal ratio of about 10.8 and the oil content is 13.6%.

EXAMPLE S-8

Following the procedure of Example S-1, a solution of 780 parts (1 equivalent) of an alkylated benzenesulfonic acid and 103 parts of the polybutenyl succinic anhydride in 350 parts of mineral oil is mixed with 640 parts (16 equivalents) of sodium hydroxide and 640 parts (20 equivalents) of methanol. This mixture is blown with carbon dioxide for about one hour at 6 cfh. During this period, the temperature increases to 95° C. and then gradually decreases to 75° C. The volatile material is stripped by blowing with nitrogen. During stripping, the temperature initially drops to 70° C. over 30 minutes and then slowly rises to 78° C. over 15 minutes. The mixture is then heated to 155° C. over 80 minutes. The stripped mixture is heated for an additional 30 minutes at 155°–160° C. and filtered. The filtrate is an oil solution of the desired basic sodium sulfonate, having a metal ratio of about 15.2. It has an oil content of 17.1%.

EXAMPLE S-9

A mixture of 584 parts (0.75 mole) of a commercial dialkyl aromatic sulfonic acid, 144 parts (0.37 mole) of a sulfurized tetrapropenyl phenol prepared as in Example 3-C , 93 parts of a polybutenyl succinic anhydride as used in Example S-1, 500 parts of xylene and 549 parts of oil is prepared and heated with stirring to 70° C. whereupon 97 parts of potassium hydroxide are added. The mixture is heated to 145° C. while azeotroping water and xylene. Additional potassium hydroxide (368 parts) is added over 10 minutes and heating is continued at about 145°–150° C. whereupon the mixture is blown with carbon dioxide at 1.5 cfh. for about 110 minutes. The volatile materials are stripped by blowing with nitrogen and slowly increasing the temperature to about 160° C. After stripping, the reaction mixture is filtered to yield an oil solution of the desired potassium sulfonate having a metal ratio of about 10.

Additional oil is added to the reaction product to provide an oil content of the final solution of 39%.

The following examples illustrate the preparation of neutral and basic alkaline earth metal salts (A-2-c).

EXAMPLE S-10

A mixture of 906 parts of an oil solution of an alkyl phenyl sulfonic acid (having a number average molecular weight of 450, 564 parts mineral oil, 600 parts toluene, 98.7 parts magnesium oxide and 120 parts water is blown with carbon dioxide at a temperature of 78°–85° C. for 7 hours at a rate of about 3 cubic feet of carbon dioxide per hour. The reaction mixture is constantly agitated throughout the carbonation. After carbonation, the reaction mixture is stripped to 165° C./20 tor and the residue filtered. The filtrate is an oil solution (34% oil) of the desired overbased magnesium sulfonate having a metal ratio of about 3.

EXAMPLE S-11

A polyisobutenyl succinic anhydride is prepared by reacting a chlorinated poly(isobutene) (having an average chlorine content of 4.3% and derived from a polyisobutene having a number average molecular weight of about 1150) with maleic anhydride at about 200° C. To a mixture of 1246 parts of this succinic anhydride and 1000 parts of toluene there is added at 25° C., 76.6 parts of barium oxide. The mixture is heated to 115° C. and 125 parts of water is added drop-wise over a period of one hour. The mixture is then allowed to reflux at 150° C. until all the barium oxide is reacted. Stripping and filtration containing the desired product.

EXAMPLE S-12

A basic calcium sulfonate having a metal ratio of about 15 is prepared by carbonation, in increments, of a mixture of calcium hydroxide, a neutral sodium petroleum sulfonate, calcium chloride, methanol and an alkyl phenol.

EXAMPLE S-13

A mixture of 323 parts of mineral oil, 4.8 parts of water, 0.74 parts of calcium chloride, 79 parts of lime, and 128 parts of methyl alcohol is prepared, and warmed to a temperature of about 50° C. To this mixture there is added 1000 parts of an alkyl phenyl sulfonic acid having a number average molecular weight of 500 with mixing. The mixture then is blown with carbon dioxide at a temperature of about 50° C. at the rate of about 5.4 pounds per hour for about 2.5 hours. After carbonation, 102 additional parts of oil are added and the mixture is stripped of volatile materials at a temperature of about 150°–155° C. at 55 mm. pressure. The residue is filtered and the filtrate is the desired oil solution of the overbased calcium sulfonate having calcium content of about 3.7% and a metal ratio of about 1.7.

EXAMPLE S-14

A mixture of 490 parts (by weight) of a mineral oil, 110 parts of water, 61 parts of heptylphenol, 340 parts of barium mahogany sulfonate, and 227 parts of barium oxide is heated at 100° C. for 0.5 hour and then to 150° C. Carbon dioxide is then bubbled into the mixture until the mixture is substantially neutral. The mixture is filtered and the filtrate found to have a sulfate ash content of 25%.

EXAMPLE S-15

A polyisobutene having a number average molecular weight of 50,000 is mixed with 10% by weight of phosphorus pentasulfide at 200° C. for 6 hours. The resulting product is hydrolyzed by treatment with steam at 160° C. to produce an acidic intermediate. The acidic intermediate is then converted to a basic salt by mixing with twice its volume of mineral oil, 2 moles of barium hydroxide and 0.7 mole of phenol and carbonating the mixture at 150° C. to produce a fluid product.

The oil solutions (A-2) used in the process of this invention comprise a major amount of hydrocarbon oil, (A-2-a) minor amounts of at least one of the dispersants (A-2-b) and optionally at least one of the metal salts (A-2-c). The esters and metal salts may each be present in amounts of from about 0.1 to about 20% by weight.

The oil solutions (A-2) also may contain other useful additives including metal dihydrocarbyl dithiophosphates, viscosity improvers, including those having dispersant or detergent properties, compositions generally referred to as friction modifiers when added to oils, etc. When included in the oil solution, these additives are present in amounts of from about 0.1 to about 20%, more generally from 0.1 to about 10% by weight.

(A-2-d) Metal Dihydrocarbyl Dithiophosphate.

In another embodiment, the oil compositions of the present invention also contain (D) at least one metal dihydrocarbyl dithiophosphate characterized by the formula

wherein $R^1$ and $R^2$ are each independently hydrocarbyl groups containing from 3 to about 13 carbon atoms, M is a metal, and n is an integer equal to the valence of M.

The oil solutions of the present invention may contain varying amounts of one or more of the above-identified metal dithiophosphates such as from about 0.01 to about 5% by weight based on the weight of the total oil solutions.

The hydrocarbyl groups $R^1$ and $R^2$ in the dithiophosphate of Formula XI may be alkyl, cycloalkyl, aralkyl or alkaryl groups, or a substantially hydrocarbon group of similar structure. By "substantially hydrocarbon" is meant hydrocarbons which contain substituent groups such as ether, ester, nitro, or halogen which do not materially affect the hydrocarbon character of the group.

Illustrative alkyl groups include isopropyl, isobutyl, n-butyl, sec-butyl, the various amyl groups, n-hexyl, methylisobutyl carbinyl, heptyl, 2-ethylhexyl, diisobutyl, isooctyl, nonyl, behenyl, decyl, dodecyl, tridecyl, etc. Illustrative alkylphenyl groups include butylphenyl, amylphenyl, heptylphenyl, butylene dimer substituted phenol, propylene tetramer-substituted phenol, etc. Cycloalkyl groups likewise are useful and these include chiefly cyclohexyl and the lower alkyl-cyclohexyl radicals. Many substituted hydrocarbon groups may also be used, e.g., chloropentyl, dichlorophenyl, and dichlorodecyl.

The phosphorodithioic acids from which the metal salts useful in this invention are prepared are well known. Examples of dihydrocarbyl phosphorodithioic acids and metal salts, and processes for preparing such acids and salts are found in, for example, U.S. Pat. Nos. 4,263,150; 4,289, 635; 4,308,154; and 4,417,990. These patents are hereby incorporated by reference for such disclosures.

The phosphorodithioic acids are prepared by the reaction of phosphorus pentasulfide with an alcohol or phenol or mixtures of alcohols. The reaction involves four moles of the alcohol or phenol per mole of phosphorus pentasulfide, and may be carried out within the temperature range from about 50° C. to about 200° C. Thus the preparation of O,O-di-n-hexyl phosphorodithioic acid involves the reaction of phosphorus pentasulfide with four moles of n-hexyl alcohol at about 100° C. for about two hours. Hydrogen sulfide is liberated and the residue is the defined acid. The preparation of the metal salt of this acid may be effected by reaction with metal oxide. Simply mixing and heating these two reactants is sufficient to cause the reaction to take place and the resulting product is sufficiently pure for the purposes of this invention.

The metal salts of dihydrocarbyl dithiophosphates which are useful in this invention include those salts containing Group I metals, Group II metals, aluminum, lead, tin, molybdenum, manganese, iron, cobalt, and nickel. The Group II metals, aluminum, iron, tin, iron, cobalt, lead, molybdenum, manganese, nickel and copper are among the preferred metals. Zinc and copper are especially useful metals.

The oil solutions useful in the present invention also may contain at least one of the materials referred to as friction modifiers in the lubricant art. Various amines, particularly tertiary amines are effective friction modifiers. Examples of tertiary amine friction modifiers include N-fatty alkyl-N,N-diethanol amines, N-fatty alkyl-N,N-diethoxy ethanol amines, etc. Such tertiary amines can be prepared by reacting a fatty alkyl amine with an appropriate number of moles of ethylene oxide. Tertiary amines derived from naturally occurring substances such as coconut oil and oleoamine are available from Armour Chemical Company under the trade designation "Ethomeen". Particular examples are the Ethomeen-C and the Ethomeen-O series.

Sulfur-containing compounds such as sulfurized $C_{12-24}$ fats, alkyl sulfides and polysulfides wherein the alkyl groups contain from 1 to 8 carbon atoms, and sulfurized polyolefins also may be included in the oil solutions of the invention. Partial fatty acid esters of polyhydric alcohols, also may be included in the oil solutions used in the invention in amounts of up to about 5 or 10% by weight. The hydroxy fatty acid esters are selected from hydroxy fatty acid esters of dihydric or polyhydric alcohols or oil-soluble oxyalkylenated derivatives thereof.

The term "fatty acid" as used in the specification and claims refers to acids which may be obtained by the hydrolysis of a naturally occurring vegetable or animal fat or oil. These acids usually contain from about 8 to about 22 carbon atoms and include, for example, caprylic acid, caproic acid, palmitic acid, stearic acid, oleic acid, linoleic acid, etc. Acids containing from 10 to 22 carbon atoms generally are preferred, and in some embodiments, those acids containing from 16 to 18 carbon atoms are especially preferred.

The polyhydric alcohols which can be utilized in the preparation of the partial fatty acids contain from 2 to about 8 or 10 hydroxyl groups, more generally from about 2 to about 4 hydroxyl groups. Examples of suitable polyhydric alcohols include ethylene glycol, propylene glycol, neopentylene glycol, glycerol, pentaerythritol, etc. Ethylene glycol and glycerol are preferred. Polyhydric alcohols containing lower alkoxy groups such as methoxy and/or ethoxy groups may be utilized in the preparation of the partial fatty acid esters.

Suitable partial fatty acid esters of polyhydric alcohols include, for example, glycol monoesters, glycerol mono- and diesters, and pentaerythritol di-and/or triesters. The partial fatty acid esters of glycerol are preferred, and of the glycerol esters, monoesters, or mixtures of monoesters and diesters are often utilized. The partial fatty acid esters of polyhydric alcohols can be prepared by methods well known in the art, such as by direct esterification of an acid with a polyol, reaction of a fatty acid with an epoxide, etc.

It is generally preferred that the partial fatty acid ester contain olefinic unsaturation, and this olefinic unsaturation usually is found in the acid moiety of the ester. In addition to natural fatty acids containing olefinic unsaturation such as oleic acid, octeneoic acids, tetradeceneoic acids, etc., can be utilized in forming the esters.

The partial fatty acid esters utilized in the oil solutions of the present invention may be present as components of a mixture containing a variety of other components such as unreacted fatty acid, fully esterified polyhydric alcohols, and other materials. Commercially available partial fatty acid esters often are mixtures which contain one or more of these components as well as mixtures of mono- and diesters of glycerol.

One method for preparing monoglycerides of fatty acids from fats and oils is described in Birnbaum U.S. Pat. No. 2,875,221. The process described in this patent is a continuous process for reacting glycerol and fats to provide a product having a high proportion of monoglyceride. Among the commercially available glycerol esters are ester mixtures containing at least about 30% by weight of monoester and generally from about 35% to about 65% by weight of monoester, about 30% to about 50% by weight of diester, and the balance in the aggregate, generally less than about 15%, is a mixture of triester, free fatty acid and other components. Specific examples of commercially available material comprising fatty acid esters of glycerol include Emery 2421 (Emery Industries, Inc.), Cap City GMO (Capital), DUR-EM 114, DUR-EM GMO, etc. (Durkee Industrial Foods, Inc.) and various materials identified under the mark MAZOL GMO (Mazer Chemicals, Inc.). Other examples of partial fatty acid esters of polyhydric alcohols may be found in K. S. Markley, Ed., *Fatty Acids*, Second Edition, Parts I and V, Interscience Publishers (1968). Numerous com- mercially available fatty acid esters of polyhydric alcohols are listed by tradename and manufacturer in McCutcheon *Emulsifiers and Detergents*, North American and International Combined Editions (1981).

Viscosity improvers can also be included in the oil solutions (A-2) used in the invention. A number of types of viscosity improvers are known in the art, and many of these are described in Ranney, *Lubricant Additives*, (Noyes Data Corporation, 1973), pp. 93–119. Illustrative viscosity improvers include various olefin polymers such as polybutene (especially containing predominantly isobutene units); ethylene-propylene copolymers; copolymers of ethylene and other low molecular weight olefins (especially alpha-olefins); terpolymers of ethylene; propylene and various dienes (especially non-conjugated dienes); polybutadiene; hydrogenated styrene-butadiene copolymers; alkylated polystyrenes; polymers of alkyl methacrylates; alkylene polyethers; and polyesters prepared from polyols, short-chain dicarboxylic acids and monobasic carboxylic acid terminators (useful predominantly in lubricants in which the lubricating oil is a synthetic ester).

One type of viscosity improver having dispersant or detergent properties comprises interpolymers being substantially free of titratable acidity and containing carboxylic ester groups in which part of the alcohol moieties have at least 8 aliphatic carbon atoms and another part have no more than 7 aliphatic carbon atoms, and also containing carbonyl-polyamino groups in which the polyamino group is derived from a compound having one primary or secondary amino group. These polymers are described in U.S. Pat. No.

3,702,300, which is incorporated by reference for such description. Preferred are interpolymers prepared by first copolymerizing styrene with maleic anhydride and subsequently esterifying a portion of the carboxylic acid groups with a mixture of primary alcohols having the numbers of carbon atoms noted above, and neutralizing the remaining carboxylic acid groups with a suitable amine. The working examples of U.S. Pat. No. 3,702,300 illustrate specific suitable polymers.

Isocyanate monomers are recovered from crude isocyanate concentrates obtained in the production of isocyanates in accordance with the process of the present invention by heating a mixture of the crude isocyanate concentrate and the above-described oil solutions at an elevated temperature whereby the isocyanate monomer is distilled from the concentrate and recovered. The residue is a liquid which can be removed easily from the heating apparatus and can be disposed of by burning. If the oil solution is not added to the isocyanate concentrate, the residue which is obtained after distillation of the isocyanate from the concentrate is a slag-like residue which is an extremely hard solid substantially insoluble in all conventional solvents. The slag-like solid is difficult to remove from the distillation apparatus, and when removed from the apparatus, presents significant disposal problems.

The incorporation of the oil solutions described above into the isocyanate concentrate prior to distillation also facilitates the distillation process by allowing higher temperatures, resulting in an increase in the yield of monomeric isocyanate distillate and recovery of a liquid residue concentrate.

The oil solutions (A-2) of the present invention can be mixed with the isocyanate concentrates in any amount, but for practical and economic reasons, the mixtures which are subject to distillation generally will contain from about 70 to about 99 parts by weight of the isocyanate concentrate (A-1) and from about 1 to about 30 parts by weight of the oil solution (A-2). More particularly, desirable results are obtained with up to about 20 parts by weight of the oil solution in 80 or more parts of the isocyanate concentrate.

The oil solutions (A-2) will comprise a major amount of the hydrocarbon oil (A-2-a) and minor amounts of the carboxylic esters (A-2-b) and/or the neutral or basic metal salts (A-2-c) described above. In particular embodiments, the oil solutions will contain from about 0.1 to about 20% by weight of the carboxylic esters (A-2-b) and from about 0.1 to about 20% by weight of at least one metal salt (A-2-c). In another embodiment, the oil solution also contains at least one metal salt of a dihydrocarbyldithiophosphoric acid (A-2-d), and the amount of said salt may range from about 0.1 to about 10% by weight. The other additives described above as being optional also may be included in the oil solutions (A-2).

Distillation of the mixture of crude isocyanate concentrate and oil solution is effected by heating the mixture to an elevated temperature sufficient to distill the isocyanate monomer from the mixture. To facilitate the distillation and reduce the temperature, the distillation preferably is accomplished at reduced pressure. The distillation temperature is regulated to provide for effective distillation of the isocyanate monomer without distillation of any of the other components of the mixture. Thus, the hydrocarbon oil (A-2-a) used in the oil solution, and any other solvents included in the components of the oil solution should have initial boiling points above the boiling point of the isocyanate monomer in the concentrate. Thus, in one embodiment, a hydrocarbon oil utilized in the formation of mixtures comprising crude tolylene diisocyanate concentrates is characterized as having an initial boiling point of at least about 200° C. at 10 mm. Hg. The boiling point of the tolylene diisocyanates is about 120° C. at 10 mm. Hg.

The following examples illustrate the oil solutions useful in the present invention.

| Oil Solution (A) | Parts/Wt. |
|---|---|
| Example 1 | |
| Citgo 350 Neutral oil (boiling point 349° C.) | 94 |
| Carboxylic ester of Ex. E-1 | 5 |
| Basic sodium sulfonate of Ex. S-1 | 1 |
| Example 2 | |
| Mineral oil (Citgo 350 Neutral) | 90 |
| Carboxylic ester of Ex. E-1 | 5 |
| Sodium salt of Ex. S-2 | 4 |
| Zinc dithiophosphate prepared from propylene tetramer-substituted phenol (containing 3.6% zinc, 3.2% phosphorus and 27% oil) | 1 |
| Example 3 | |
| Citgo 350 Neutral oil | 94 |
| Carboxylic ester of Ex. E-12 | 5 |
| Basic calcium alkylated benzene sulfonate (44% oil, 15.5% calcium and metal ratio of 20) | 1 |
| Example 4 | |
| Mineral oil (Citgo 350 Neutral) | 90 |
| Carboxylic ester of Ex. E-12 | 5 |
| Sodium salt of Ex. S-2 | 4 |
| Basic calcium alkylated benzene sulfonate (44% oil, 15.5% calcium and metal ratio of 20) | 1 |
| Example 5 | |
| Citgo 350 Neutral oil | 94 |
| Carboxylic ester of Ex. E-12 | 5 |
| Basic magnesium alkylated benzene sulfonate (32% oil, metal ratio of 14.7) | 1 |
| Example 6 | |
| Citgo 350 Neutral oil | 90 |
| Carboxylic ester of Ex. E-12 | 5 |
| Basic calcium alkylated benzene sulfonate (44% oil, 15.5% calcium and metal ratio of 20) | 4 |
| Zinc dithiophosphate prepared from propylene tetramer-substituted phenol (containing 3.6% zinc, 3.2% phosphorus and 27% oil) | 1 |

The process of the present invention is illustrated by the following examples.

EXAMPLE A

A mixture comprising 75 parts of a concentrate of dicyclohexylmethane-4,4'-diisocyanate (obtained by the phosgenation of the corresponding bis(aminocyclohexyl) methane in o-dichlorobenzene) and 25 parts of the oil solution from Example 1 is charged to a distillation apparatus. The mixture is heated to a temperature of 150° C. at 0.5 mm Hg. The monomeric isocyanate distills from the mixture and is collected. When the rate of distillation becomes negligible, the residue in the reaction vessel is cooled to 100° C. and is recoverable as a pumpable liquid.

EXAMPLE B

The process of Example A is repeated except that the isocyanate concentrate is mixed with 25 parts of the solution of Example 3.

EXAMPLE C

The procedure of Example A is repeated except that the concentrate used in this example is a tolylene diisocyanate concentrate obtained by phosgenation of 2,4-diamino toluene.

EXAMPLE D

The procedure of Example A is repeated except that the isocyanate concentrate is a tolylene diisocyanate mixture obtained by phosgenation of a mixture comprising 80 parts of 2,4-diamino toluene and 20 parts of 2,6-diamino toluene.

EXAMPLE E

The procedure of Example A is repeated except that the isocyanate concentrate is a concentrate obtained by reaction of 1 mole of 2,4-diamino toluene with 2 moles of phosgene, and the oil solution is the solution of Example 3.

EXAMPLE F

The procedure of Example E is repeated except that the oil solution used is the solution of Example 6.

While the invention has been explained in relation to its preferred embodiments, it is to be understood that various modifications thereof will become apparent to those skilled in the art upon reading the specification. Therefore, -it is to be understood that the invention disclosed herein is intended to cover such modifications as fall within the scope of the appended claims.

We claim:

1. A process for the separation and recovery of isocyanate monomers from isocyanate concentrates formed in the production of isocyanates and comprising a volatile isocyanate monomer and by-products which comprises the steps of:
   (A) preparing a mixture comprising
      (A-1) the isocyanate concentrate; and
      (A-2) an oil solution comprising:
         (A-2-a) a major amount of hydrocarbon oil, and
         (A-2-b) a minor amount of at least one dispersant selected from the group consisting of (1) a carboxylic dispersant prepared by reacting a substituted carboxylic acid or derivative thereof with an amine having present within its structure at least one >NH group, or a basic inorganic material, (2) an amine dispersant prepared by reacting an aliphatic or alicyclic halide with an amine, (3) a Mannich dispersant, and (4) a product obtained by post-treating (1), (2), or (3) with a member selected from the group consisting of urea, thiourea, carbon disulfide, an aldehyde, a ketone, a carboxylic acid, a hydrocarbon-substituted anhydride, a nitrile, an epoxide, a boron compound, and a phosphorus compound, provided that the dispersant is not an ester obtained by reacting at least one substituted succinic acylating agent with at least one alcohol of the general formula $$R_3(OH)_m \qquad (I)$$

wherein $R_3$ is a monovalent or polyvalent organic group joined to the OH groups through carbon bonds, and m is an integer of from 1 to about 10, and
   (B) heating the mixture to an elevated temperature whereby isocyanate monomer is distilled and recovered, leaving a liquid residue wherein the oil solution (A-2) also contains
      (A-2-c) a minor amount of at least one neutral or basic alkali metal or alkaline earth metal salt of at least one acidic organic compound.

2. The process for the separation and recovery of isocyanate monomers from isocyanate concentrates formed in the production of isocyanates and comprising a volatile isocyanate monomer and by-products which comprises the steps of:
   (A) preparing a mixture comprising
      (A-1) the isocyanate concentrate; and
      (A-2) an oil solution comprising:
         (A-2-a) a major amount of hydrocarbon oil, and
         (A-2-b) a minor amount of at least one dispersant selected from the group consisting of (1) a carboxylic dispersant prepared by reacting a substituted carboxylic acid or derivative thereof with an amine having present within its structure at least one >NH group, or a basic inorganic material, (2) an amine dispersant prepared by reacting an aliphatic or alicyclic halide with an amine, (3) a Mannich dispersant, and (4) a product obtained by post-treating (1), (2), or (3) with a member selected from the group consisting of urea, thiourea, carbon disulfide, an aldehyde, a ketone, a carboxylic acid, a hydrocarbon-substituted anhydride, a nitrile, an epoxide, a boron compound, and a phosphorus compound, provided that the dispersant is not an ester obtained by reacting at least one substituted succinic acylating agent with at least one alcohol of the general formula $$R_3(OH)_m \qquad (I)$$

wherein $R_3$ is a monovalent or polyvalent organic group joined to the OH groups through carbon bonds, and m is an integer of from 1 to about 10, and
   (B) heating the mixture to an elevated temperature whereby isocyanate monomer is distilled and recovered, leaving a liquid residue wherein the oil solution (A-2) also contains (A-2-d) a minor amount of at least one metal salt of a dihydrocarbyldithiophosphoric acid wherein the metal is a Group II metal, aluminum, tin, iron, cobalt, lead, molybdenum, manganese, nickel or copper.

* * * * *